United States Patent
Ball et al.

(10) Patent No.: US 11,840,700 B2
(45) Date of Patent: Dec. 12, 2023

(54) MULTI FUNCTIONAL TOXINS

(71) Applicant: Monsanto Technology LLC, St. Louis, MO (US)

(72) Inventors: Timothy K. Ball, Foristell, MO (US); Artem G. Evdokimov, Orchard Park, NY (US); Larry A. Gilbertson, Somerville, MA (US); Victor M. Guzov, Cambridge, MA (US); Jeffrey A. Haas, Chesterfield, MO (US); Qing Huai, Winchester, MA (US); Sergey Ivashuta, Ballwin, MO (US); Melissa M. Kemp, Medford, MA (US); Yifei Kong, Chesterfield, MO (US); Thomas M. Malvar, North Stonington, CT (US); Byron V. Olsen, Ballwin, MO (US); Parthasarathy Ramaseshadri, St. Louis, MO (US); Brian E. Weiner, St. Louis, MO (US)

(73) Assignee: Monsanto Technology LLC, St. Louis, MO (US)

(*) Notice: Subject to any disclaimer, the term of this patent is extended or adjusted under 35 U.S.C. 154(b) by 0 days.

(21) Appl. No.: 15/217,695

(22) Filed: Jul. 22, 2016

(65) Prior Publication Data
US 2017/0029844 A1    Feb. 2, 2017

Related U.S. Application Data

(60) Provisional application No. 62/328,543, filed on Apr. 27, 2016, provisional application No. 62/196,249, filed on Jul. 23, 2015.

(51) Int. Cl.
| C12N 15/82 | (2006.01) |
| A01N 37/44 | (2006.01) |
| C07K 14/325 | (2006.01) |
| A01N 37/46 | (2006.01) |

(52) U.S. Cl.
CPC ......... *C12N 15/8286* (2013.01); *A01N 37/44* (2013.01); *A01N 37/46* (2013.01); *C07K 14/325* (2013.01); *Y02A 40/146* (2018.01)

(58) Field of Classification Search
CPC ................................................. C12N 15/8286
See application file for complete search history.

(56) References Cited

U.S. PATENT DOCUMENTS

| 8,034,997 B2* | 10/2011 | Bogdanova ........ C12N 15/8286 514/4.5 |
| 8,269,069 B1* | 9/2012 | Narva ................ C12N 15/8286 800/302 |
| 8,735,560 B1 | 5/2014 | English et al. |
| 9,090,906 B2* | 7/2015 | Soberon-Chavez ........ C07K 14/325 |
| 9,512,187 B2* | 12/2016 | Je ......................... A01N 63/50 |
| 9,556,453 B2* | 1/2017 | Meade ................... A01N 63/02 |
| 9,796,983 B2* | 10/2017 | Narva .................... A01G 22/00 |
| 2010/0186123 A1* | 7/2010 | Pardo-Lopez ..... C12N 15/8286 800/295 |
| 2010/0221238 A1 | 9/2010 | Flexner et al. |
| 2014/0073582 A1 | 3/2014 | Olmos Soto et al. |
| 2015/0055802 A1 | 2/2015 | Tu et al. |

OTHER PUBLICATIONS

Ho et al (Crop Science vol. 46 Mar.-Apr. 2006). (Year: 2006).*
De Maagd et al (Appl Environ. Microbiol 65:4369-4374, 1999) (Year: 1999).*
Aronson et al ((FEMS Microbiol. Lett. 2001, 195:1-8) (Year: 2001).*
Bohorova et al (Theor Appl Genet (2001) 103:817-826) (Year: 2001).*
Tounsi et al (J. Appl. MicrobioL 95:23-28; 2003) (Year: 2003).*
De MDe Maagd, Ruud A., et al. "Identification of Bacillus thuringiensisdelta-endotoxin Cry1C domain III amino acid residues involved in insect specificity." Appl. Environ. Microbiol. 65.10 (1999): 4369-4374. (Year: 1999).*
Aronson, Arthur I., and Yechiel Shai. "Why Bacillus thuringiensis insecticidal toxins are so effective: unique features of their mode of action." FEMS Microbiology Letters 195.1 (2001): 1-8. (Year: 2001).*
Tounsi, S., N. Zouari, and S. Jaoua. "Cloning and study of the expression of a novel cry1Ia-type gene from *Bacillus thuringiensis* subsp. kurstaki." Journal of applied microbiology 95.1 (2003): 23-28. (Year: 2003).*
GenBank Accession AAU87037.1, available online on Feb. 25, 2005 (Year: 2005).*
Liu et al (Protein Engineering, Design and Selection, vol. 19, Issue 3, Mar. 1, 2006, pp. 107-111). (Year: 2006).*
Kim, Yang-Su, et al. "Mutagenesis of Bacillus thuringiensis cry1Ac gene and its insecticidal activity against Plutella xylostella and Ostrinia furnacalis." Biological Control 47.2 (2008): 222-227. (Year: 2008).*
Shan, Shiping, et al. "A Cry1Ac toxin variant generated by directed evolution has enhanced toxicity against Lepidopteran insects." Current microbiology 62.2 (2011): 358-365. (Year: 2011).*
Packer, Michael S., and David R. Liu. "Methods for the directed evolution of proteins." Nature Reviews Genetics 16.7 (2015): 379-394. (Year: 2015).*
Flagel et al., 2018, Sci Rep 8, 7255. https://doi.org/10.1038/s41598-018-25491-9.*
Heckel, 2020, Arch. Insect. Biochem. Physiol. 104:e21673, https://doi.org/10.1002/arch.21673.*
Wang et al., 2018, Reg. Toxicol. Pharmacol. 99: 50-60.*

(Continued)

*Primary Examiner* — Anne Kubelik
(74) *Attorney, Agent, or Firm* — Dentons US LLP; Timothy K. Ball

(57) ABSTRACT

Pesticidal proteins are provided that combine two or more modes of action into a single molecule. These pesticidal proteins therefor exhibit greater efficacy and/or durability of resistance, for the purposes of pest control, and can be utilized for pest control by provision in the diet of a pest organism, or by topical application to crop plants and/or pests. Methods and compositions for producing and using such proteins are also provided.

10 Claims, No Drawings

Specification includes a Sequence Listing.

(56) References Cited

OTHER PUBLICATIONS

International Search Report for PC/US2016/043691 dated Oct. 21, 2016.

Badran et al., "Continuous evolution of *Bacillus thuringiensis* toxins overcomes insect resistance," *Nature*, 533:58-63, 2016.

Baum et al., "Cotton plants expressing a hemipteran-active *Bacillus thuringiensis* crystal protein impact the development and survival of *Lygus hesperus* (Hemiptera: Miridae) nymphs," *J Econ Entomol*, 105:616-624, 2012.

Esvelt et al., "A system for the continuous directed evolution of biomolecules," *Nature*, 472:499-503, 2011.

Vaughn et al., "The establishment of two cell lines from the insect *Spodoptera frugiperda* (Lepidoptera; Noctuidae)" In Vitro, 13:213-217, 1977.

Extended European Search Report regarding Europe Application No. 16828648, dated Jan. 1, 2019.

Flannagan et al., "Identification, cloning and expression of a CrylAb cadherin receptor from European corn borer, *Ostrinia nubilalis* (Hubner) (Lepidoptera:Crambidae)", Insect Biochemistry and Molecular Biology, 35(1):33-40, 2005.

Fujii et al., "Cry1Aa binding to the cadherin receptor does not require conserved amino acid sequences in the domain II loops", Bioscience Reports, 33(1):103-112, 2013.

Likitvivatanavong et al., "Multiple Receptors as Targets of Cry Toxins in Mosquitoes", Journal of Agriculture and Food Chemistry, 59(7):2829-2838, 2011.

Pardo-Lopez et al., "Bacillus thuringiensis insecticidal three-domain Cry toxins: mode of action, insect resistance and consequences for crop protection", 37(1):3-22, 2013.

Tanaka et al., "The ATP-binding cassette transporter subfamily C member 2 in Bombyx mori larvae is a functional receptor for Cry toxins from Bacillus thuringiensis",FEBS Journal, 280(8):1782-1794, 2013.

\* cited by examiner

```
                        SEQUENCE LISTING

<160> NUMBER OF SEQ ID NOS: 13

<210> SEQ ID NO 1
<211> LENGTH: 1178
<212> TYPE: PRT
<213> ORGANISM: Bacillus thuringiensis

<400> SEQUENCE: 1

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220
```

```
Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
            275                 280                 285

Arg Ser Ile Arg Ser Pro His Leu Met Asp Ile Leu Asn Ser Ile Thr
290                 295                 300

Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
            435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
            515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
            565                 570                 575

Asn Ala Phe Thr Ser Ser Leu Gly Asn Ile Val Gly Val Arg Asn Phe
            580                 585                 590

Ser Gly Thr Ala Gly Val Ile Ile Asp Arg Phe Glu Phe Ile Pro Val
            595                 600                 605

Thr Ala Thr Leu Glu Ala Glu Tyr Asn Leu Glu Arg Ala Gln Lys Ala
            610                 615                 620

Val Asn Ala Leu Phe Thr Ser Thr Asn Gln Leu Gly Leu Lys Thr Asn
625                 630                 635                 640
```

-continued

```
Val Thr Asp Tyr His Ile Asp Gln Val Ser Asn Leu Val Thr Tyr Leu
                645                 650                 655

Ser Asp Glu Phe Cys Leu Asp Glu Lys Arg Glu Leu Ser Glu Lys Val
            660                 665                 670

Lys His Ala Lys Arg Leu Ser Asp Glu Arg Asn Leu Leu Gln Asp Ser
        675                 680                 685

Asn Phe Lys Asp Ile Asn Arg Gln Pro Glu Arg Gly Trp Gly Gly Ser
    690                 695                 700

Thr Gly Ile Thr Ile Gln Gly Gly Asp Asp Val Phe Lys Glu Asn Tyr
705                 710                 715                 720

Val Thr Leu Ser Gly Thr Phe Asp Glu Cys Tyr Pro Thr Tyr Leu Tyr
                725                 730                 735

Gln Lys Ile Asp Glu Ser Lys Leu Lys Ala Phe Thr Arg Tyr Gln Leu
            740                 745                 750

Arg Gly Tyr Ile Glu Asp Ser Gln Asp Leu Glu Ile Tyr Leu Ile Arg
        755                 760                 765

Tyr Asn Ala Lys His Glu Thr Val Asn Val Pro Gly Thr Gly Ser Leu
    770                 775                 780

Trp Pro Leu Ser Thr Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
                805                 810                 815

Arg Asp Gly Glu Lys Cys Ala His His Ser His Phe Ser Leu Asp
            820                 825                 830

Ile Asp Val Gly Cys Thr Asp Leu Asn Glu Asp Leu Gly Val Trp Val
        835                 840                 845

Ile Phe Lys Ile Lys Thr Gln Asp Gly His Ala Arg Leu Gly Asn Leu
    850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
                885                 890                 895

Glu Thr Asn Ile Val Tyr Lys Glu Ala Lys Glu Ser Val Asp Ala Leu
            900                 905                 910

Phe Val Asn Ser Gln Tyr Asp Gln Leu Gln Ala Asp Thr Asn Ile Ala
        915                 920                 925

Met Ile His Ala Ala Asp Lys Arg Val His Ser Ile Arg Glu Ala Tyr
    930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
                965                 970                 975

Asn Val Ile Lys Asn Gly Asp Phe Asn Asn Gly Leu Ser Cys Trp Asn
            980                 985                 990

Val Lys Gly His Val Asp Val Glu  Glu Gln Asn Asn Gln  Arg Ser Val
        995                 1000                1005

Leu Val  Val Pro Glu Trp Glu  Ala Glu Val Ser Gln  Glu Val Arg
        1010                1015                1020

Val Cys  Pro Gly Arg Gly Tyr  Ile Leu Arg Val Thr  Ala Tyr Lys
        1025                1030                1035

Glu Gly  Tyr Gly Glu Gly Cys  Val Thr Ile His Glu  Ile Glu Asn
        1040                1045                1050
```

```
Asn Thr Asp Glu Leu Lys Phe Ser Asn Cys Val Glu Glu Ile
    1055                1060                1065

Tyr Pro Asn Asn Thr Val Thr Cys Asn Asp Tyr Thr Val Asn Gln
    1070                1075                1080

Glu Glu Tyr Gly Gly Ala Tyr Thr Ser Arg Asn Arg Gly Tyr Asn
    1085                1090                1095

Glu Ala Pro Ser Val Pro Ala Asp Tyr Ala Ser Val Tyr Glu Glu
    1100                1105                1110

Lys Ser Tyr Thr Asp Gly Arg Arg Glu Asn Pro Cys Glu Phe Asn
    1115                1120                1125

Arg Gly Tyr Arg Asp Tyr Thr Pro Leu Pro Val Gly Tyr Val Thr
    1130                1135                1140

Lys Glu Leu Glu Tyr Phe Pro Glu Thr Asp Lys Val Trp Ile Glu
    1145                1150                1155

Ile Gly Glu Thr Glu Gly Thr Phe Ile Val Asp Ser Val Glu Leu
    1160                1165                1170

Leu Leu Met Glu Glu
    1175

<210> SEQ ID NO 2
<211> LENGTH: 1178
<212> TYPE: PRT
<213> ORGANISM: Artificial Sequence
<220> FEATURE:
<223> OTHER INFORMATION: synthetic

<400> SEQUENCE: 2

Met Asp Asn Asn Pro Asn Ile Asn Glu Cys Ile Pro Tyr Asn Trp Leu
1               5                   10                  15

Ser Asn Pro Glu Val Glu Val Leu Gly Gly Glu Arg Ile Glu Thr Gly
                20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220
```

```
Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Arg Ser Ile Arg Ser Pro His Leu Met Asp Ile Leu Asn Ser Ile Asn
    290                 295                 300

Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Glu Ala Pro Gln Gln Arg Ile Val Ala
            340                 345                 350

Gln Leu Gly Gln Gly Val Tyr Arg Ile Leu Ser Ser Thr Leu Tyr Arg
        355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Lys Phe Ser Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Leu Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu Glu Arg Ala Gln Lys Ala
    610                 615                 620

Val Asn Ala Leu Phe Thr Ser Thr Asn Gln Leu Gly Leu Lys Thr Asn
625                 630                 635                 640
```

```
Val Thr Asp Tyr His Ile Asp Gln Val Ser Asn Leu Val Thr Tyr Leu
            645                 650                 655

Ser Asp Glu Phe Cys Leu Asp Glu Lys Arg Glu Leu Ser Glu Lys Val
            660                 665                 670

Lys His Ala Lys Arg Leu Ser Asp Glu Arg Asn Leu Leu Gln Asp Ser
            675                 680                 685

Asn Phe Lys Asp Ile Asn Arg Gln Pro Glu Arg Gly Trp Gly Gly Ser
            690                 695                 700

Thr Gly Ile Thr Ile Gln Gly Gly Asp Asp Val Phe Lys Glu Asn Tyr
705                 710                 715                 720

Val Thr Leu Ser Gly Thr Phe Asp Glu Cys Tyr Pro Thr Tyr Leu Tyr
            725                 730                 735

Gln Lys Ile Asp Glu Ser Lys Leu Lys Ala Phe Thr Arg Tyr Gln Leu
            740                 745                 750

Arg Gly Tyr Ile Glu Asp Ser Gln Asp Leu Glu Ile Tyr Leu Ile Arg
            755                 760                 765

Tyr Asn Ala Lys His Glu Thr Val Asn Val Pro Gly Thr Gly Ser Leu
            770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
            805                 810                 815

Arg Asp Gly Glu Lys Cys Ala His His Ser His His Phe Ser Leu Asp
            820                 825                 830

Ile Asp Val Gly Cys Thr Asp Leu Asn Glu Asp Leu Gly Val Trp Val
            835                 840                 845

Ile Phe Lys Ile Lys Thr Gln Asp Gly His Ala Arg Leu Gly Asn Leu
            850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
            885                 890                 895

Glu Thr Asn Ile Val Tyr Lys Glu Ala Lys Glu Ser Val Asp Ala Leu
            900                 905                 910

Phe Val Asn Ser Gln Tyr Asp Gln Leu Gln Ala Asp Thr Asn Ile Ala
            915                 920                 925

Met Ile His Ala Ala Asp Lys Arg Val His Ser Ile Arg Glu Ala Tyr
            930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
            965                 970                 975

Asn Val Ile Lys Asn Gly Asp Phe Asn Asn Gly Leu Ser Cys Trp Asn
            980                 985                 990

Val Lys Gly His Val Asp Val Glu  Glu Gln Asn Asn Gln  Arg Ser Val
            995                 1000                1005

Leu Val  Val Pro Glu Trp Glu  Ala Glu Val Ser Gln  Glu Val Arg
     1010                 1015                1020

Val Cys  Pro Gly Arg Gly Tyr  Ile Leu Arg Val Thr  Ala Tyr Lys
     1025                 1030                1035

Glu Gly  Tyr Gly Glu Gly Cys  Val Thr Ile His Glu  Ile Glu Asn
     1040                 1045                1050
```

Asn Thr Asp Glu Leu Lys Phe Ser Asn Cys Val Glu Glu Ile
    1055                1060                1065

Tyr Pro Asn Asn Thr Val Thr Cys Asn Asp Tyr Thr Val Asn Gln
    1070                1075                1080

Glu Glu Tyr Gly Gly Ala Tyr Thr Ser Arg Asn Arg Gly Tyr Asn
    1085                1090                1095

Glu Ala Pro Ser Val Pro Ala Asp Tyr Ala Ser Val Tyr Glu Glu
    1100                1105                1110

Lys Ser Tyr Thr Asp Gly Arg Arg Glu Asn Pro Cys Glu Phe Asn
    1115                1120                1125

Arg Gly Tyr Arg Asp Tyr Thr Pro Leu Pro Val Gly Tyr Val Thr
    1130                1135                1140

Lys Glu Leu Glu Tyr Phe Pro Glu Thr Asp Lys Val Trp Ile Glu
    1145                1150                1155

Ile Gly Glu Thr Glu Gly Thr Phe Ile Val Asp Ser Val Glu Leu
    1160                1165                1170

Leu Leu Met Glu Glu
    1175

<210> SEQ ID NO 3
<211> LENGTH: 1178
<212> TYPE: PRT
<213> ORGANISM: Artificial sequence
<220> FEATURE:
<223> OTHER INFORMATION: synthetic

<400> SEQUENCE: 3

Met Asp Asn Asn Pro Asn Ile Asn Glu Cys Ile Pro Tyr Asn Trp Leu
1               5                   10                  15

Ser Asn Pro Glu Val Glu Val Leu Gly Gly Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Ser Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220

-continued

```
Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Asp Ile Glu
        275                 280                 285

Arg Ser Ile Arg Ser Pro His Leu Met Asp Ile Leu Asn Ser Ile Asn
    290                 295                 300

Ile Tyr Thr Asp Ala His Arg Gly Tyr Tyr Trp Ser Gly His Gln
305                 310                 315                 320

Ile Lys Ala Ser Pro Val Gly Phe Ser Gly Pro Gly Phe Thr Phe Pro
                325                 330                 335

Leu Tyr Gly Thr Met Gly Asn Glu Ala Pro Gln Gln Arg Ile Val Ala
            340                 345                 350

His Leu Gly Gln Gly Val Tyr Arg Ile Leu Ser Ser Thr Leu Tyr Arg
        355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Lys Phe Ser Asn
    450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
    530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
                565                 570                 575

Asn Ala Phe Thr Ser Leu Leu Gly Asn Ile Val Gly Val Arg Asn Phe
            580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu Glu Arg Ala Gln Lys Ala
    610                 615                 620

Val Asn Ala Leu Phe Thr Ser Thr Asn Gln Leu Gly Leu Lys Thr Asn
625                 630                 635                 640
```

-continued

Val Thr Asp Tyr His Ile Asp Gln Val Ser Asn Leu Val Thr Tyr Leu
            645                 650                 655

Ser Asp Glu Phe Cys Leu Asp Glu Lys Arg Glu Leu Ser Glu Lys Val
        660                 665                 670

Lys His Ala Lys Arg Leu Ser Asp Glu Arg Asn Leu Leu Gln Asp Ser
    675                 680                 685

Asn Phe Lys Asp Ile Asn Arg Gln Pro Glu Arg Gly Trp Gly Gly Ser
690                 695                 700

Thr Gly Ile Thr Ile Gln Gly Gly Asp Asp Val Phe Lys Glu Asn Tyr
705                 710                 715                 720

Val Thr Leu Ser Gly Thr Phe Asp Glu Cys Tyr Pro Thr Tyr Leu Tyr
            725                 730                 735

Gln Lys Ile Asp Glu Ser Lys Leu Lys Ala Phe Thr Arg Tyr Gln Leu
        740                 745                 750

Arg Gly Tyr Ile Glu Asp Ser Gln Asp Leu Glu Ile Tyr Leu Ile Arg
    755                 760                 765

Tyr Asn Ala Lys His Glu Thr Val Asn Val Pro Gly Thr Gly Ser Leu
770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
            805                 810                 815

Arg Asp Gly Glu Lys Cys Ala His His Ser His Phe Ser Leu Asp
        820                 825                 830

Ile Asp Val Gly Cys Thr Asp Leu Asn Glu Asp Leu Gly Val Trp Val
    835                 840                 845

Ile Phe Lys Ile Lys Thr Gln Asp Gly His Ala Arg Leu Gly Asn Leu
850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
            885                 890                 895

Glu Thr Asn Ile Val Tyr Lys Glu Ala Lys Glu Ser Val Asp Ala Leu
        900                 905                 910

Phe Val Asn Ser Gln Tyr Asp Gln Leu Gln Ala Asp Thr Asn Ile Ala
    915                 920                 925

Met Ile His Ala Ala Asp Lys Arg Val His Ser Ile Arg Glu Ala Tyr
930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
            965                 970                 975

Asn Val Ile Lys Asn Gly Asp Phe Asn Asn Gly Leu Ser Cys Trp Asn
        980                 985                 990

Val Lys Gly His Val Asp Val Glu Glu Gln Asn Asn Gln Arg Ser Val
    995                 1000                1005

Leu Val Val Pro Glu Trp Glu Ala Glu Val Ser Gln Glu Val Arg
    1010                1015                1020

Val Cys Pro Gly Arg Gly Tyr Ile Leu Arg Val Thr Ala Tyr Lys
    1025                1030                1035

Glu Gly Tyr Gly Glu Gly Cys Val Thr Ile His Glu Ile Glu Asn
    1040                1045                1050

```
Asn Thr Asp Glu Leu Lys Phe Ser Asn Cys Val Glu Glu Glu Ile
    1055                1060                1065

Tyr Pro Asn Asn Thr Val Thr Cys Asn Asp Tyr Thr Val Asn Gln
    1070                1075                1080

Glu Glu Tyr Gly Gly Ala Tyr Thr Ser Arg Asn Arg Gly Tyr Asn
    1085                1090                1095

Glu Ala Pro Ser Val Pro Asp Tyr Ala Ser Val Tyr Glu Glu
    1100                1105                1110

Lys Ser Tyr Thr Asp Gly Arg Arg Glu Asn Pro Cys Glu Phe Asn
    1115                1120                1125

Arg Gly Tyr Arg Asp Tyr Thr Pro Leu Pro Val Gly Tyr Val Thr
    1130                1135                1140

Lys Glu Leu Glu Tyr Phe Pro Glu Thr Asp Lys Val Trp Ile Glu
    1145                1150                1155

Ile Gly Glu Thr Glu Gly Thr Phe Ile Val Asp Ser Val Glu Leu
    1160                1165                1170

Leu Leu Met Glu Glu
    1175

<210> SEQ ID NO 4
<211> LENGTH: 1178
<212> TYPE: PRT
<213> ORGANISM: Artificial sequence
<220> FEATURE:
<223> OTHER INFORMATION: synthetic

<400> SEQUENCE: 4

Met Asp Asn Asn Pro Asn Ile Asn Glu Cys Ile Pro Tyr Asn Trp Leu
1               5                   10                  15

Ser Asn Pro Glu Val Glu Val Leu Gly Gly Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
            100                 105                 110

Ser Phe Arg Glu Trp Glu Ala Asp Pro Thr Asn Pro Ala Leu Arg Glu
        115                 120                 125

Glu Met Arg Ile Gln Phe Asn Asp Met Asn Ser Ala Leu Thr Thr Ala
    130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
        195                 200                 205

Arg Trp Tyr Asn Thr Gly Leu Glu Arg Val Trp Gly Pro Asp Ser Arg
    210                 215                 220
```

```
Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
            245                 250                 255

Ile Arg Thr Val Ser Gln Leu Thr Arg Glu Ile Tyr Thr Asn Pro Val
        260                 265                 270

Leu Glu Asn Phe Asp Gly Ser Phe Arg Gly Ser Ala Gln Gly Ile Glu
    275                 280                 285

Arg Ser Ile Arg Ser Pro His Leu Met Asp Ile Leu Asn Ser Ile Asn
290                 295                 300

Ile Tyr Thr Asp Ala His Arg Gly Tyr Tyr Trp Ser Gly His Gln
305                 310                 315                 320

Ile Lys Ala Ser Pro Val Gly Phe Ser Gly Pro Glu Phe Thr Phe Pro
                325                 330                 335

Leu Tyr Gly Thr Met Gly Asn Glu Ala Pro Gln Gln Arg Ile Val Ala
            340                 345                 350

His Leu Gly Gln Gly Val Tyr Arg Ile Leu Ser Ser Thr Leu Tyr Arg
        355                 360                 365

Arg Pro Phe Asn Ile Gly Ile Asn Asn Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Lys Phe Ser Asn
450                 455                 460

Ile Ile Ala Ser Asp Ser Ile Thr Gln Ile Pro Ala Val Lys Gly Asn
465                 470                 475                 480

Phe Leu Phe Asn Gly Ser Val Ile Ser Gly Pro Gly Phe Thr Gly Gly
                485                 490                 495

Asp Leu Val Arg Leu Asn Ser Ser Gly Asn Asn Ile Gln Asn Arg Gly
            500                 505                 510

Tyr Ile Glu Val Pro Ile His Phe Pro Ser Thr Ser Thr Arg Tyr Arg
        515                 520                 525

Val Arg Val Arg Tyr Ala Ser Val Thr Pro Ile His Leu Asn Val Asn
530                 535                 540

Trp Gly Asn Ser Ser Ile Phe Ser Asn Thr Val Pro Ala Thr Ala Thr
545                 550                 555                 560

Ser Leu Asp Asn Leu Gln Ser Ser Asp Phe Gly Tyr Phe Glu Ser Ala
            565                 570                 575

Asn Ala Phe Thr Ser Leu Leu Gly Asn Ile Val Gly Val Arg Asn Phe
        580                 585                 590

Ser Gly Thr Ala Gly Val Ile Ile Asp Arg Phe Glu Phe Ile Pro Val
        595                 600                 605

Thr Ala Thr Leu Glu Ala Glu Tyr Asn Leu Glu Arg Ala Gln Lys Ala
        610                 615                 620

Val Asn Ala Leu Phe Thr Ser Thr Asn Gln Leu Gly Leu Lys Thr Asn
625                 630                 635                 640
```

```
Val Thr Asp Tyr His Ile Asp Gln Val Ser Asn Leu Val Thr Tyr Leu
                645                 650                 655

Ser Asp Glu Phe Cys Leu Asp Glu Lys Arg Glu Leu Ser Glu Lys Val
            660                 665                 670

Lys His Ala Lys Arg Leu Ser Asp Glu Arg Asn Leu Leu Gln Asp Ser
        675                 680                 685

Asn Phe Lys Asp Ile Asn Arg Gln Pro Glu Arg Gly Trp Gly Gly Ser
    690                 695                 700

Thr Gly Ile Thr Ile Gln Gly Gly Asp Asp Val Phe Lys Glu Asn Tyr
705                 710                 715                 720

Val Thr Leu Ser Gly Thr Phe Asp Glu Cys Tyr Pro Thr Tyr Leu Tyr
            725                 730                 735

Gln Lys Ile Asp Glu Ser Lys Leu Lys Ala Phe Thr Arg Tyr Gln Leu
        740                 745                 750

Arg Gly Tyr Ile Glu Asp Ser Gln Asp Leu Glu Ile Tyr Leu Ile Arg
    755                 760                 765

Tyr Asn Ala Lys His Glu Thr Val Asn Val Pro Gly Thr Gly Ser Leu
770                 775                 780

Trp Pro Leu Ser Ala Gln Ser Pro Ile Gly Lys Cys Gly Glu Pro Asn
785                 790                 795                 800

Arg Cys Ala Pro His Leu Glu Trp Asn Pro Asp Leu Asp Cys Ser Cys
            805                 810                 815

Arg Asp Gly Glu Lys Cys Ala His His Ser His Phe Ser Leu Asp
        820                 825                 830

Ile Asp Val Gly Cys Thr Asp Leu Asn Glu Asp Leu Gly Val Trp Val
    835                 840                 845

Ile Phe Lys Ile Lys Thr Gln Asp Gly His Ala Arg Leu Gly Asn Leu
850                 855                 860

Glu Phe Leu Glu Glu Lys Pro Leu Val Gly Glu Ala Leu Ala Arg Val
865                 870                 875                 880

Lys Arg Ala Glu Lys Lys Trp Arg Asp Lys Arg Glu Lys Leu Glu Trp
            885                 890                 895

Glu Thr Asn Ile Val Tyr Lys Glu Ala Lys Glu Ser Val Asp Ala Leu
        900                 905                 910

Phe Val Asn Ser Gln Tyr Asp Gln Leu Gln Ala Asp Thr Asn Ile Ala
    915                 920                 925

Met Ile His Ala Ala Asp Lys Arg Val His Ser Ile Arg Glu Ala Tyr
930                 935                 940

Leu Pro Glu Leu Ser Val Ile Pro Gly Val Asn Ala Ala Ile Phe Glu
945                 950                 955                 960

Glu Leu Glu Gly Arg Ile Phe Thr Ala Phe Ser Leu Tyr Asp Ala Arg
            965                 970                 975

Asn Val Ile Lys Asn Gly Asp Phe Asn Asn Gly Leu Ser Cys Trp Asn
        980                 985                 990

Val Lys Gly His Val Asp Val Glu Glu Gln Asn Asn Gln Arg Ser Val
    995                 1000                1005

Leu Val Val Pro Glu Trp Glu Ala Glu Val Ser Gln Glu Val Arg
    1010                1015                1020

Val Cys Pro Gly Arg Gly Tyr Ile Leu Arg Val Thr Ala Tyr Lys
    1025                1030                1035

Glu Gly Tyr Gly Glu Gly Cys Val Thr Ile His Glu Ile Glu Asn
    1040                1045                1050
```

```
Asn Thr Asp Glu Leu Lys Phe Ser Asn Cys Val Glu Glu Glu Ile
    1055                1060                1065

Tyr Pro Asn Asn Thr Val Thr Cys Asn Asp Tyr Thr Val Asn Gln
    1070                1075                1080

Glu Glu Tyr Gly Gly Ala Tyr Thr Ser Arg Asn Arg Gly Tyr Asn
    1085                1090                1095

Glu Ala Pro Ser Val Pro Ala Asp Tyr Ala Ser Val Tyr Glu Glu
    1100                1105                1110

Lys Ser Tyr Thr Asp Gly Arg Arg Glu Asn Pro Cys Glu Phe Asn
    1115                1120                1125

Arg Gly Tyr Arg Asp Tyr Thr Pro Leu Pro Val Gly Tyr Val Thr
    1130                1135                1140

Lys Glu Leu Glu Tyr Phe Pro Glu Thr Asp Lys Val Trp Ile Glu
    1145                1150                1155

Ile Gly Glu Thr Glu Gly Thr Phe Ile Val Asp Ser Val Glu Leu
    1160                1165                1170

Leu Leu Met Glu Glu
    1175

<210> SEQ ID NO 5
<211> LENGTH: 798
<212> TYPE: PRT
<213> ORGANISM: Bacillus thuringiensis

<400> SEQUENCE: 5

Met Gln Arg Met Ile Ile Val Asp Asn Asn Lys Leu Asn Val Arg Ala
1               5                   10                  15

Leu Pro Ser Phe Ile Asp Tyr Phe Asn Gly Ile Tyr Gly Phe Ala Thr
                20                  25                  30

Gly Ile Lys Asp Ile Met Gly Met Ile Phe Lys Thr Asp Thr Gly Gly
            35                  40                  45

Ser Asn Leu Thr Leu Asp Glu Ile Leu Lys Asn Gln Asn Leu Leu Asn
    50                  55                  60

Asp Ile Ser Gly Lys Leu Asp Gly Ile Asn Gly Asp Leu Gly Asp Leu
65                  70                  75                  80

Ile Ala Gln Gly Asn Leu Asn Ser Glu Leu Ala Lys Glu Leu Leu Lys
                85                  90                  95

Ile Ser Asn Glu Gln Asn Gln Met Leu Asn His Val Asn Ala Gln Leu
            100                 105                 110

Asn Ala Ile Asn Ser Thr Leu Asn Ile Tyr Leu Pro Lys Ile Thr Ser
        115                 120                 125

Met Leu Asn Glu Val Met Lys Gln Asn His Val Leu Ser Leu Gln Ile
    130                 135                 140

Glu Phe Leu Ser Lys Gln Leu Gln Glu Ile Ser Asp Lys Leu Asp Ile
145                 150                 155                 160

Ile Asn Leu Asn Val Leu Ile Asn Ser Thr Leu Thr Glu Ile Thr Pro
                165                 170                 175

Ala Tyr Gln Arg Ile Lys Tyr Val Asn Glu Lys Phe Asp Glu Leu Thr
            180                 185                 190

Ser Thr Val Glu Lys Asn Pro Lys Ser Tyr Gln Asp Asn Val Thr Lys
        195                 200                 205

Glu Val Ile Glu Asn Leu Asn Glu Leu Thr Glu Leu Ala Lys Ser Val
    210                 215                 220
```

-continued

```
Thr Lys Asn Asp Met Asp Ser Phe Glu Phe Tyr Leu Gln Thr Phe His
225                 230                 235                 240

Asp Val Met Thr Gly Asn Asn Leu Phe Gly Arg Ser Ala Leu Lys Thr
            245                 250                 255

Ala Ser Glu Leu Ile Thr Lys Glu Asn Val Thr Thr Arg Gly Ser Glu
                260                 265                 270

Ile Gly Lys Val Tyr Asn Phe Leu Ile Val Leu Thr Ser Leu Gln Ala
            275                 280                 285

Lys Ala Phe Leu Thr Leu Thr Ala Cys Arg Lys Leu Leu Gly Leu Thr
290                 295                 300

Asp Ile Asp Tyr Thr Gln Ile Met Asn His His Ile Asp Gly Gln Lys
305                 310                 315                 320

Arg Glu Phe Arg Ile Asn Ile Leu Pro Thr Leu Ser Asn Asn Phe Ser
                325                 330                 335

Asn Pro Ser Tyr Ser Lys Asn Arg Gly Ser Asp Ile Asp Asp Pro Ile
            340                 345                 350

Val Val Leu Glu Ala Ala Pro Gly Tyr Ala Leu Ile Gly Phe Glu Ile
                355                 360                 365

Leu Asn Asp Pro Leu Pro Ile Leu Lys Gly Tyr Gln Ala Arg Leu Lys
370                 375                 380

Pro Asn Tyr Gln Val Asp Arg Glu Ser Met Ser Glu Thr Ile Tyr Gly
385                 390                 395                 400

Asp Ile His Lys Leu Phe Cys Pro Lys Gln Leu Glu Gln Lys Tyr Tyr
                405                 410                 415

Ile Lys Asp Ile Glu Phe Pro Glu Gly Tyr Val Ile Thr Lys Ile Val
            420                 425                 430

Phe Glu Lys Arg Leu Asn Gln Leu Gly Tyr Glu Val Thr Ala Asn Phe
                435                 440                 445

Tyr Asp Pro Ser Thr Gly Ser Ile Asp Leu Asn Lys Val Lys Val Glu
            450                 455                 460

Ser Trp Lys Glu Lys Ser Cys Glu Glu Asp Ser Cys Glu Asp Glu Tyr
465                 470                 475                 480

Ser Ile Ile Lys Ala Glu Thr Asp Gly Ile Tyr Met Pro Leu Gly Val
                485                 490                 495

Val Ser Glu Thr Phe Leu Thr Pro Ile Tyr Gly Phe Gly Leu Thr Val
                500                 505                 510

Asp Glu Lys Asn Gln Lys Ile Thr Leu Thr Gly Lys Ser Tyr Leu Arg
            515                 520                 525

Glu Ser Leu Leu Glu Thr Asp Leu Leu Asn Asn Glu Thr Tyr Leu Ile
530                 535                 540

Ala Ser Pro Asp Gly Tyr Ile Ser Ser Ile Val Glu Asn Trp Asn Ile
545                 550                 555                 560

Thr Ser Asp Asn Thr Gly Ser Trp Arg Ala Asn Asn Asn Ala Phe
                565                 570                 575

Val Asp Lys Ala Asp Thr Ile Lys Gly Ser Ser Leu Tyr Thr His
            580                 585                 590

Lys Asp Gly Glu Phe Ser Gln Phe Ile Gly Asn Lys Leu Lys Pro Lys
                595                 600                 605

Thr Asn Tyr Val Ile Gln Tyr Val Ile Lys Gly Arg Pro Ala Ile Tyr
            610                 615                 620

Leu Lys Asn Asn Lys Asp Thr Leu Phe Glu Asp Thr Lys Asn Asn Phe
625                 630                 635                 640
```

-continued

```
Ser Asp Phe Gln Thr Val Thr Lys Lys Phe Asn Ser Gly Val Asn Pro
                645                 650                 655

Ser Glu Ile Tyr Phe Leu Phe Lys Asn Gln Ser Glu Tyr Glu Ala Trp
            660                 665                 670

Gly Asn Asn Phe Ile Ile Leu Glu Ile Lys Ser Leu Glu Phe Leu Pro
        675                 680                 685

Gln Met Leu Lys Pro Glu Asp Trp Ile Pro Ser Gly Asn Val Gln Met
    690                 695                 700

Lys Asp Gly Gly Arg Leu Glu Ile Leu Gly Asp Gly Tyr Phe Lys Gln
705                 710                 715                 720

Phe Ile Lys Leu Glu Asn Asp Ser Thr Tyr His Leu Arg Leu Ser Val
                725                 730                 735

Lys Gly Thr Gly Arg Val Ser Ile Ile Asp Glu Ser Lys Tyr Leu Leu
            740                 745                 750

Phe Val Asn Val Lys Asp Glu Asp Leu Thr Arg Val Ile Lys Asn Thr
        755                 760                 765

Ser Ser Lys Gly Glu Cys Phe Ile Ala Leu Glu Gly Thr Tyr Val Glu
    770                 775                 780

Asn Ser Ser Thr Ile Phe Ser Asn Val Ser Ile Val Lys Glu
785                 790                 795
```

<210> SEQ ID NO 6
<211> LENGTH: 12
<212> TYPE: PRT
<213> ORGANISM: Artificial sequence
<220> FEATURE:
<223> OTHER INFORMATION: synthetic

<400> SEQUENCE: 6

```
Val Asp Trp Trp Ser Pro Phe Tyr Asp Arg Leu Lys
1               5                   10
```

<210> SEQ ID NO 7
<211> LENGTH: 807
<212> TYPE: PRT
<213> ORGANISM: Artificial sequence
<220> FEATURE:
<223> OTHER INFORMATION: synthetic

<400> SEQUENCE: 7

```
Met Gln Arg Met Ile Ile Val Asp Asn Asn Lys Leu Asn Val Arg Ala
1               5                   10                  15

Leu Pro Ser Phe Ile Asp Tyr Phe Asn Gly Ile Tyr Gly Phe Ala Thr
            20                  25                  30

Gly Ile Lys Asp Ile Met Gly Met Ile Phe Lys Thr Asp Thr Gly Gly
        35                  40                  45

Ser Asn Leu Thr Leu Asp Glu Ile Leu Lys Asn Gln Asn Leu Leu Asn
    50                  55                  60

Asp Ile Ser Gly Lys Leu Asp Gly Ile Asn Gly Asp Leu Gly Asp Leu
65                  70                  75                  80

Ile Ala Gln Gly Asn Leu Asn Ser Glu Leu Ala Lys Glu Leu Leu Lys
                85                  90                  95

Ile Ser Asn Glu Gln Asn Gln Met Leu Asn His Val Asn Ala Gln Leu
            100                 105                 110

Asn Ala Ile Asn Ser Thr Leu Asn Ile Tyr Leu Pro Lys Ile Thr Ser
        115                 120                 125

Met Leu Asn Glu Val Met Lys Gln Asn His Val Leu Ser Leu Gln Ile
    130                 135                 140
```

```
Glu Phe Leu Ser Lys Gln Leu Gln Glu Ile Ser Asp Lys Leu Asp Ile
145                 150                 155                 160

Ile Asn Leu Asn Val Leu Ile Asn Ser Thr Leu Thr Glu Ile Thr Pro
            165                 170                 175

Ala Tyr Gln Arg Ile Lys Tyr Val Asn Glu Lys Phe Asp Glu Leu Thr
        180                 185                 190

Ser Thr Val Glu Lys Asn Pro Lys Ser Tyr Gln Asp Asn Val Thr Lys
    195                 200                 205

Glu Val Ile Glu Asn Leu Asn Glu Leu Thr Glu Leu Ala Lys Ser Val
210                 215                 220

Thr Lys Asn Asp Met Asp Ser Phe Glu Phe Tyr Leu Gln Thr Phe His
225                 230                 235                 240

Asp Val Met Thr Gly Asn Asn Leu Phe Gly Arg Ser Ala Leu Lys Thr
                245                 250                 255

Ala Ser Glu Leu Ile Thr Lys Glu Asn Val Thr Thr Arg Gly Ser Glu
            260                 265                 270

Ile Gly Lys Val Tyr Asn Phe Leu Ile Val Leu Thr Ser Leu Gln Ala
        275                 280                 285

Lys Ala Phe Leu Thr Leu Thr Ala Cys Arg Lys Leu Leu Gly Leu Thr
290                 295                 300

Asp Ile Asp Tyr Thr Gln Ile Met Asn His His Ile Asp Gly Gln Lys
305                 310                 315                 320

Arg Glu Phe Arg Ile Asn Ile Leu Pro Thr Leu Ser Asn Asn Phe Ser
                325                 330                 335

Asn Pro Ser Tyr Ser Lys Asn Arg Gly Ser Asp Ile Asp Pro Ile
            340                 345                 350

Val Val Leu Glu Ala Ala Pro Gly Tyr Ala Leu Ile Gly Phe Glu Ile
            355                 360                 365

Leu Asn Asp Pro Leu Pro Ile Leu Lys Gly Tyr Gln Ala Arg Leu Lys
370                 375                 380

Pro Asn Tyr Gln Val Asp Arg Glu Ser Met Ser Glu Thr Ile Tyr Gly
385                 390                 395                 400

Asp Ile His Lys Leu Phe Cys Pro Lys Gln Leu Glu Gln Lys Tyr Tyr
                405                 410                 415

Ile Lys Asp Ile Glu Phe Pro Gly Tyr Val Ile Thr Lys Ile Val
        420                 425                 430

Phe Glu Lys Arg Leu Asn Gln Leu Gly Tyr Glu Val Thr Ala Asn Phe
            435                 440                 445

Tyr Asp Pro Ser Thr Gly Ser Ile Asp Leu Asn Lys Val Lys Val Glu
    450                 455                 460

Ser Trp Lys Glu Lys Ser Cys Glu Glu Asp Ser Cys Glu Asp Glu Tyr
465                 470                 475                 480

Ser Ile Ile Lys Ala Glu Thr Asp Gly Ile Tyr Met Pro Leu Gly Val
            485                 490                 495

Val Ser Glu Thr Phe Leu Thr Pro Ile Tyr Gly Phe Gly Leu Thr Val
        500                 505                 510

Asp Glu Lys Asn Gln Lys Ile Thr Leu Thr Gly Lys Ser Tyr Leu Arg
    515                 520                 525

Glu Ser Leu Leu Glu Thr Asp Leu Leu Asn Asn Glu Thr Tyr Leu Ile
530                 535                 540

Ala Ser Pro Asp Gly Tyr Ile Ser Ser Ile Val Glu Asn Trp Asn Ile
545                 550                 555                 560
```

```
Thr Ser Asp Asn Thr Gly Ser Trp Arg Ala Asn Asn Asn Ala Phe
            565                 570                 575

Val Asp Lys Ala Asp Thr Ile Lys Gly Ser Ser Leu Tyr Thr His
            580                 585                 590

Lys Asp Gly Glu Phe Ser Gln Phe Ile Gly Asn Lys Leu Lys Pro Lys
        595                 600                 605

Thr Asn Tyr Val Ile Gln Tyr Val Ile Lys Gly Arg Pro Ala Ile Tyr
    610                 615                 620

Leu Lys Asn Asn Lys Asp Thr Leu Phe Glu Asp Thr Lys Asn Asn Phe
625                 630                 635                 640

Ser Asp Phe Gln Thr Val Thr Lys Lys Phe Asn Ser Gly Val Asn Pro
            645                 650                 655

Ser Glu Ile Tyr Phe Leu Phe Lys Asn Gln Ser Glu Tyr Glu Ala Trp
            660                 665                 670

Gly Asn Asn Phe Ile Ile Leu Glu Ile Lys Ser Leu Glu Phe Leu Pro
        675                 680                 685

Gln Met Leu Lys Pro Glu Asp Trp Ile Pro Ser Gly Asn Val Gln Met
    690                 695                 700

Lys Asp Gly Gly Arg Leu Glu Ile Leu Gly Asp Gly Tyr Phe Lys Gln
705                 710                 715                 720

Phe Ile Lys Leu Glu Asn Asp Ser Thr Tyr His Leu Arg Leu Ser Val
            725                 730                 735

Lys Gly Thr Gly Arg Val Ser Ile Ile Asp Val Asp Trp Ser Pro
            740                 745                 750

Phe Tyr Asp Arg Leu Lys Tyr Leu Leu Phe Val Asn Val Lys Asp Glu
        755                 760                 765

Asp Leu Thr Arg Val Ile Lys Asn Thr Ser Ser Lys Gly Glu Cys Phe
    770                 775                 780

Ile Ala Leu Glu Gly Thr Tyr Val Glu Asn Ser Ser Thr Ile Phe Ser
785                 790                 795                 800

Asn Val Ser Ile Val Lys Glu
            805
```

```
<210> SEQ ID NO 8
<211> LENGTH: 1177
<212> TYPE: PRT
<213> ORGANISM: Artificial sequence
<220> FEATURE:
<223> OTHER INFORMATION: synthetic

<400> SEQUENCE: 8
```

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
            85                  90                  95

Ile Ser Arg Leu Glu Gly Leu Ser Asn Leu Tyr Gln Ile Tyr Ala Glu
        100                 105                 110
```

```
Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
            195                 200                 205

Arg Trp Tyr Asn Thr Gly Leu Glu Arg Val Trp Gly Pro Asp Ser Arg
        210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
        355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
450                 455                 460

Ile Ile Ala Ser Asp Ser Ile Thr Gln Ile Pro Leu Val Lys Ala His
465                 470                 475                 480

Thr Leu Gln Ser Gly Thr Thr Val Val Arg Gly Pro Gly Phe Thr Gly
                485                 490                 495

Gly Asp Ile Leu Arg Arg Thr Ser Gly Gly Pro Phe Ala Tyr Thr Ile
            500                 505                 510

Val Asn Ile Asn Gly Gln Leu Pro Gln Arg Tyr Arg Ala Arg Ile Arg
        515                 520                 525
```

Tyr Ala Ser Thr Thr Asn Leu Arg Ile Tyr Val Thr Val Ala Gly Glu
        530                 535                 540

Arg Ile Phe Ala Gly Gln Phe Asn Lys Thr Met Asp Thr Gly Asp Pro
545                 550                 555                 560

Leu Thr Phe Gln Ser Phe Ser Tyr Ala Thr Ile Asn Thr Ala Phe Thr
                565                 570                 575

Phe Pro Met Ser Gln Ser Ser Phe Thr Val Gly Ala Asp Thr Phe Ser
            580                 585                 590

Ser Gly Asn Glu Val Tyr Ile Asp Arg Phe Glu Leu Ile Pro Val Thr
        595                 600                 605

Ala Thr Leu Glu Ala Glu Tyr Asn Leu Glu Arg Ala Gln Lys Ala Val
610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Tyr Leu Ser
                645                 650                 655

Asp Glu Phe Cys Leu Asp Glu Lys Arg Glu Leu Ser Glu Lys Val Lys
            660                 665                 670

His Ala Lys Arg Leu Ser Asp Glu Arg Asn Leu Leu Gln Asp Ser Asn
        675                 680                 685

Phe Lys Asp Ile Asn Arg Gln Pro Glu Arg Gly Trp Gly Gly Ser Thr
690                 695                 700

Gly Ile Thr Ile Gln Gly Gly Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
            740                 745                 750

Gly Tyr Ile Glu Asp Ser Gln Asp Leu Glu Ile Tyr Ser Ile Arg Tyr
        755                 760                 765

Asn Ala Lys His Glu Thr Val Asn Val Pro Gly Thr Gly Ser Leu Trp
770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
            820                 825                 830

Asp Val Gly Cys Thr Asp Leu Asn Glu Asp Leu Gly Val Trp Val Ile
        835                 840                 845

Phe Lys Ile Lys Thr Gln Asp Gly His Ala Arg Leu Gly Asn Leu Glu
850                 855                 860

Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Gln Leu Gln Ala Asp Thr Asn Ile Ala Met
        915                 920                 925

Ile His Ala Ala Asp Lys Arg Val His Ser Ile Arg Glu Ala Tyr Leu
930                 935                 940

```
Pro Glu Leu Ser Val Ile Pro Gly Val Asn Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn Gln Arg Ser Val Leu
        995                 1000                1005

Val Val Pro Glu Trp Glu Ala Glu Val Ser Gln Glu Val Arg Val
    1010                1015                1020

Cys Pro Gly Arg Gly Tyr Ile Leu Arg Val Thr Ala Tyr Lys Glu
    1025                1030                1035

Gly Tyr Gly Glu Gly Cys Val Thr Ile His Glu Ile Glu Asn Asn
    1040                1045                1050

Thr Asp Glu Leu Lys Phe Ser Asn Cys Val Glu Glu Glu Ile Tyr
    1055                1060                1065

Pro Asn Asn Thr Val Thr Cys Asn Asp Tyr Thr Val Asn Gln Glu
    1070                1075                1080

Glu Tyr Gly Gly Ala Tyr Thr Ser Arg Asn Arg Gly Tyr Asn Glu
    1085                1090                1095

Ala Pro Ser Val Pro Ala Asp Tyr Ala Ser Val Tyr Glu Glu Lys
    1100                1105                1110

Ser Tyr Thr Asp Gly Arg Arg Glu Asn Pro Cys Glu Phe Asn Arg
    1115                1120                1125

Gly Tyr Arg Asp Tyr Thr Pro Leu Pro Val Gly Tyr Val Thr Lys
    1130                1135                1140

Glu Leu Glu Tyr Phe Pro Glu Thr Asp Lys Val Trp Ile Glu Ile
    1145                1150                1155

Gly Glu Thr Glu Gly Thr Phe Ile Val Asp Ser Val Glu Leu Leu
    1160                1165                1170

Leu Met Glu Glu
    1175

<210> SEQ ID NO 9
<211> LENGTH: 12
<212> TYPE: PRT
<213> ORGANISM: Artificial sequence
<220> FEATURE:
<223> OTHER INFORMATION: synthetic

<400> SEQUENCE: 9

Ser Asp Tyr Gly Trp Trp Arg Pro Phe Gln Pro Gly
1               5                   10

<210> SEQ ID NO 10
<211> LENGTH: 1186
<212> TYPE: PRT
<213> ORGANISM: Artificial sequence
<220> FEATURE:
<223> OTHER INFORMATION: synthetic

<400> SEQUENCE: 10

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45
```

```
Glu Phe Val Pro Gly Ala Gly Phe Leu Gly Leu Val Asp Ile Ile
 50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Phe Ala Arg Asn Gln Ala
                 85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
        195                 200                 205

Arg Trp Tyr Asn Thr Gly Leu Glu Arg Val Trp Gly Pro Asp Ser Arg
210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
        275                 280                 285

Gly Ser Ile Arg Ser Pro His Leu Met Asp Ile Leu Asn Ser Ile Thr
290                 295                 300

Ile Tyr Thr Asp Ala His Arg Gly Glu Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Ser Asp Tyr Gly Trp Trp Arg Pro Phe Gln Pro
            340                 345                 350

Gly Ala Pro Gln Gln Arg Ile Val Ala Gln Leu Gly Gln Gly Val Tyr
        355                 360                 365

Arg Thr Leu Ser Ser Thr Leu Tyr Arg Arg Pro Phe Asn Ile Gly Ile
370                 375                 380

Asn Asn Gln Gln Leu Ser Val Leu Asp Gly Thr Glu Phe Ala Tyr Gly
385                 390                 395                 400

Thr Ser Ser Asn Leu Pro Ser Ala Val Tyr Arg Lys Ser Gly Thr Val
                405                 410                 415

Asp Ser Leu Asp Glu Ile Pro Pro Gln Asn Asn Asn Val Pro Pro Arg
            420                 425                 430

Gln Gly Phe Ser His Arg Leu Ser His Val Ser Met Phe Arg Ser Gly
        435                 440                 445

Phe Ser Asn Ser Ser Val Ser Ile Ile Arg Ala Pro Met Phe Ser Trp
450                 455                 460
```

-continued

Ile His Arg Ser Ala Glu Phe Asn Asn Ile Ile Ala Ser Asp Ser Ile
465                 470                 475                 480

Thr Gln Ile Pro Leu Val Lys Ala His Thr Leu Gln Ser Gly Thr Thr
            485                 490                 495

Val Val Arg Gly Pro Gly Phe Thr Gly Gly Asp Ile Leu Arg Arg Thr
        500                 505                 510

Ser Gly Gly Pro Phe Ala Tyr Thr Ile Val Asn Ile Asn Gly Gln Leu
    515                 520                 525

Pro Gln Arg Tyr Arg Ala Arg Ile Arg Tyr Ala Ser Thr Thr Asn Leu
    530                 535                 540

Arg Ile Tyr Val Thr Val Ala Gly Glu Arg Ile Phe Ala Gly Gln Phe
545                 550                 555                 560

Asn Lys Thr Met Asp Thr Gly Asp Pro Leu Thr Phe Gln Ser Phe Ser
            565                 570                 575

Tyr Ala Thr Ile Asn Thr Ala Phe Thr Phe Pro Met Ser Gln Ser Ser
            580                 585                 590

Phe Thr Val Gly Ala Asp Thr Phe Ser Ser Gly Asn Glu Val Tyr Ile
        595                 600                 605

Asp Arg Phe Glu Leu Ile Pro Val Thr Ala Thr Leu Glu Ala Glu Tyr
    610                 615                 620

Asn Leu Glu Arg Ala Gln Lys Ala Val Asn Ala Leu Phe Thr Ser Thr
625                 630                 635                 640

Asn Gln Leu Gly Leu Lys Thr Asn Val Thr Asp Tyr His Ile Asp Gln
            645                 650                 655

Val Ser Asn Leu Val Thr Tyr Leu Ser Asp Glu Phe Cys Leu Asp Glu
        660                 665                 670

Lys Arg Glu Leu Ser Glu Lys Val Lys His Ala Lys Arg Leu Ser Asp
    675                 680                 685

Glu Arg Asn Leu Leu Gln Asp Ser Asn Phe Lys Asp Ile Asn Arg Gln
    690                 695                 700

Pro Glu Arg Gly Trp Gly Gly Ser Thr Gly Ile Thr Ile Gln Gly Gly
705                 710                 715                 720

Asp Asp Val Phe Lys Glu Asn Tyr Val Thr Leu Ser Gly Thr Phe Asp
            725                 730                 735

Glu Cys Tyr Pro Thr Tyr Leu Tyr Gln Lys Ile Asp Glu Ser Lys Leu
            740                 745                 750

Lys Ala Phe Thr Arg Tyr Gln Leu Arg Gly Tyr Ile Glu Asp Ser Gln
        755                 760                 765

Asp Leu Glu Ile Tyr Ser Ile Arg Tyr Asn Ala Lys His Glu Thr Val
    770                 775                 780

Asn Val Pro Gly Thr Gly Ser Leu Trp Pro Leu Ser Ala Gln Ser Pro
785                 790                 795                 800

Ile Gly Lys Cys Gly Glu Pro Asn Arg Cys Ala Pro His Leu Glu Trp
            805                 810                 815

Asn Pro Asp Leu Asp Cys Ser Cys Arg Asp Gly Glu Lys Cys Ala His
            820                 825                 830

His Ser His His Phe Ser Leu Asp Ile Asp Val Gly Cys Thr Asp Leu
        835                 840                 845

Asn Glu Asp Leu Gly Val Trp Val Ile Phe Lys Ile Lys Thr Gln Asp
    850                 855                 860

Gly His Ala Arg Leu Gly Asn Leu Glu Phe Leu Glu Glu Lys Pro Leu
865                 870                 875                 880

-continued

```
Val Gly Glu Ala Leu Ala Arg Val Lys Arg Ala Glu Lys Lys Trp Arg
                885                 890                 895

Asp Lys Arg Glu Lys Leu Glu Trp Glu Thr Asn Ile Val Tyr Lys Glu
            900                 905                 910

Ala Lys Glu Ser Val Asp Ala Leu Phe Val Asn Ser Gln Tyr Asp Gln
        915                 920                 925

Leu Gln Ala Asp Thr Asn Ile Ala Met Ile His Ala Ala Asp Lys Arg
    930                 935                 940

Val His Ser Ile Arg Glu Ala Tyr Leu Pro Glu Leu Ser Val Ile Pro
945                 950                 955                 960

Gly Val Asn Ala Ala Ile Phe Glu Glu Leu Glu Gly Arg Ile Phe Thr
                965                 970                 975

Ala Phe Ser Leu Tyr Asp Ala Arg Asn Val Ile Lys Asn Gly Asp Phe
            980                 985                 990

Asn Asn Gly Leu Ser Cys Trp Asn Val Lys Gly His Val Asp Val Glu
        995                 1000                1005

Glu Gln Asn Asn Gln Arg Ser Val Leu Val Val Pro Glu Trp Glu
    1010                1015                1020

Ala Glu Val Ser Gln Glu Val Arg Val Cys Pro Gly Arg Gly Tyr
    1025                1030                1035

Ile Leu Arg Val Thr Ala Tyr Lys Glu Gly Tyr Gly Glu Gly Cys
    1040                1045                1050

Val Thr Ile His Glu Ile Glu Asn Asn Thr Asp Glu Leu Lys Phe
    1055                1060                1065

Ser Asn Cys Val Glu Glu Glu Ile Tyr Pro Asn Asn Thr Val Thr
    1070                1075                1080

Cys Asn Asp Tyr Thr Val Asn Gln Glu Glu Tyr Gly Gly Ala Tyr
    1085                1090                1095

Thr Ser Arg Asn Arg Gly Tyr Asn Glu Ala Pro Ser Val Pro Ala
    1100                1105                1110

Asp Tyr Ala Ser Val Tyr Glu Glu Lys Ser Tyr Thr Asp Gly Arg
    1115                1120                1125

Arg Glu Asn Pro Cys Glu Phe Asn Arg Gly Tyr Arg Asp Tyr Thr
    1130                1135                1140

Pro Leu Pro Val Gly Tyr Val Thr Lys Glu Leu Glu Tyr Phe Pro
    1145                1150                1155

Glu Thr Asp Lys Val Trp Ile Glu Ile Gly Glu Thr Glu Gly Thr
    1160                1165                1170

Phe Ile Val Asp Ser Val Glu Leu Leu Leu Met Glu Glu
    1175                1180                1185
```

<210> SEQ ID NO 11
<211> LENGTH: 1190
<212> TYPE: PRT
<213> ORGANISM: Artificial sequence
<220> FEATURE:
<223> OTHER INFORMATION: synthetic

<400> SEQUENCE: 11

```
Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
        35                  40                  45
```

Glu Phe Val Pro Gly Ala Gly Phe Val Leu Gly Leu Val Asp Ile Ile
 50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Phe Ala Arg Asn Gln Ala
                 85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
        130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Ser Ala Gln Gly Ile Glu
            275                 280                 285

Arg Ser Ile Arg Ser Pro His Leu Met Asp Ile Leu Asn Ser Ile Thr
        290                 295                 300

Ile Tyr Thr Asp Ala His Arg Gly Tyr Tyr Trp Ser Gly His Gln
305                 310                 315                 320

Ile Met Ala Ser Pro Val Gly Phe Ser Gly Pro Glu Phe Thr Phe Pro
                325                 330                 335

Leu Tyr Gly Thr Met Gly Asn Val Asp Trp Trp Ser Pro Phe Tyr Asp
            340                 345                 350

Arg Leu Lys Ala Ala Pro Gln Arg Ile Val Ala Gln Leu Gly Gln
        355                 360                 365

Gly Val Tyr Arg Thr Leu Ser Ser Thr Leu Tyr Arg Arg Pro Phe Asn
370                 375                 380

Ile Gly Ile Asn Asn Gln Gln Leu Ser Val Leu Asp Gly Thr Glu Phe
385                 390                 395                 400

Ala Tyr Gly Thr Ser Ser Asn Leu Pro Ser Ala Val Tyr Arg Lys Ser
                405                 410                 415

Gly Thr Val Asp Ser Leu Asp Glu Ile Pro Pro Gln Asn Asn Asn Val
            420                 425                 430

Pro Pro Arg Gln Gly Phe Ser His Arg Leu Ser His Val Ser Met Phe
        435                 440                 445

Arg Ser Gly Phe Ser Asn Ser Ser Val Ser Ile Ile Arg Ala Pro Met
    450                 455                 460

```
Phe Ser Trp Ile His Arg Ser Ala Glu Phe Asn Asn Ile Ile Ala Ser
465                 470                 475                 480

Asp Ser Ile Thr Gln Ile Pro Ala Val Lys Gly Asn Phe Leu Phe Asn
            485                 490                 495

Gly Ser Val Ile Ser Gly Pro Gly Phe Thr Gly Gly Asp Leu Val Arg
                500                 505                 510

Leu Asn Ser Ser Gly Asn Asn Ile Gln Asn Arg Gly Tyr Ile Glu Val
            515                 520                 525

Pro Ile His Phe Pro Ser Ser Thr Arg Tyr Arg Val Arg Val Arg
    530                 535                 540

Tyr Ala Ser Val Thr Pro Ile His Leu Asn Val Asn Trp Gly Asn Ser
545                 550                 555                 560

Ser Ile Phe Ser Asn Thr Val Pro Ala Thr Ala Thr Ser Leu Asp Asn
                565                 570                 575

Leu Gln Ser Ser Asp Phe Gly Tyr Phe Glu Ser Ala Asn Ala Phe Thr
            580                 585                 590

Ser Ser Leu Gly Asn Ile Val Gly Val Arg Asn Phe Ser Gly Thr Ala
        595                 600                 605

Gly Val Ile Ile Asp Arg Phe Glu Phe Ile Pro Val Thr Ala Thr Leu
    610                 615                 620

Glu Ala Glu Tyr Asn Leu Glu Arg Ala Gln Lys Ala Val Asn Ala Leu
625                 630                 635                 640

Phe Thr Ser Thr Asn Gln Leu Gly Leu Lys Thr Asn Val Thr Asp Tyr
                645                 650                 655

His Ile Asp Gln Val Ser Asn Leu Val Thr Tyr Leu Ser Asp Glu Phe
            660                 665                 670

Cys Leu Asp Glu Lys Arg Glu Leu Ser Glu Lys Val Lys His Ala Lys
        675                 680                 685

Arg Leu Ser Asp Glu Arg Asn Leu Leu Gln Asp Ser Asn Phe Lys Asp
    690                 695                 700

Ile Asn Arg Gln Pro Glu Arg Gly Trp Gly Gly Ser Thr Gly Ile Thr
705                 710                 715                 720

Ile Gln Gly Gly Asp Asp Val Phe Lys Glu Asn Tyr Val Thr Leu Ser
                725                 730                 735

Gly Thr Phe Asp Glu Cys Tyr Pro Thr Tyr Leu Tyr Gln Lys Ile Asp
            740                 745                 750

Glu Ser Lys Leu Lys Ala Phe Thr Arg Tyr Gln Leu Arg Gly Tyr Ile
        755                 760                 765

Glu Asp Ser Gln Asp Leu Glu Ile Tyr Leu Ile Arg Tyr Asn Ala Lys
    770                 775                 780

His Glu Thr Val Asn Val Pro Gly Thr Gly Ser Leu Trp Pro Leu Ser
785                 790                 795                 800

Ala Gln Ser Pro Ile Gly Lys Cys Gly Glu Pro Asn Arg Cys Ala Pro
                805                 810                 815

His Leu Glu Trp Asn Pro Asp Leu Asp Cys Ser Cys Arg Asp Gly Glu
            820                 825                 830

Lys Cys Ala His His Ser His His Phe Ser Leu Asp Ile Asp Val Gly
        835                 840                 845

Cys Thr Asp Leu Asn Glu Asp Leu Gly Val Trp Val Ile Phe Lys Ile
    850                 855                 860

Lys Thr Gln Asp Gly His Ala Arg Leu Gly Asn Leu Glu Phe Leu Glu
865                 870                 875                 880
```

Glu Lys Pro Leu Val Gly Glu Ala Leu Ala Arg Val Lys Arg Ala Glu
                885                 890                 895

Lys Lys Trp Arg Asp Lys Arg Glu Lys Leu Glu Trp Glu Thr Asn Ile
            900                 905                 910

Val Tyr Lys Glu Ala Lys Glu Ser Val Asp Ala Leu Phe Val Asn Ser
        915                 920                 925

Gln Tyr Asp Gln Leu Gln Ala Asp Thr Asn Ile Ala Met Ile His Ala
    930                 935                 940

Ala Asp Lys Arg Val His Ser Ile Arg Glu Ala Tyr Leu Pro Glu Leu
945                 950                 955                 960

Ser Val Ile Pro Gly Val Asn Ala Ala Ile Phe Glu Glu Leu Glu Gly
                965                 970                 975

Arg Ile Phe Thr Ala Phe Ser Leu Tyr Asp Ala Arg Asn Val Ile Lys
            980                 985                 990

Asn Gly Asp Phe Asn Asn Gly Leu Ser Cys Trp Asn Val Lys Gly His
        995                 1000                1005

Val Asp Val Glu Glu Gln Asn Asn Gln Arg Ser Val Leu Val Val
    1010                1015                1020

Pro Glu Trp Glu Ala Glu Val Ser Gln Glu Val Arg Val Cys Pro
    1025                1030                1035

Gly Arg Gly Tyr Ile Leu Arg Val Thr Ala Tyr Lys Glu Gly Tyr
    1040                1045                1050

Gly Glu Gly Cys Val Thr Ile His Glu Ile Glu Asn Asn Thr Asp
    1055                1060                1065

Glu Leu Lys Phe Ser Asn Cys Val Glu Glu Ile Tyr Pro Asn
    1070                1075                1080

Asn Thr Val Thr Cys Asn Asp Tyr Thr Val Asn Gln Glu Glu Tyr
    1085                1090                1095

Gly Gly Ala Tyr Thr Ser Arg Asn Arg Gly Tyr Asn Glu Ala Pro
    1100                1105                1110

Ser Val Pro Ala Asp Tyr Ala Ser Val Tyr Glu Glu Lys Ser Tyr
    1115                1120                1125

Thr Asp Gly Arg Arg Glu Asn Pro Cys Glu Phe Asn Arg Gly Tyr
    1130                1135                1140

Arg Asp Tyr Thr Pro Leu Pro Val Gly Tyr Val Thr Lys Glu Leu
    1145                1150                1155

Glu Tyr Phe Pro Glu Thr Asp Lys Val Trp Ile Glu Ile Gly Glu
    1160                1165                1170

Thr Glu Gly Thr Phe Ile Val Asp Ser Val Glu Leu Leu Leu Met
    1175                1180                1185

Glu Glu
    1190

<210> SEQ ID NO 12
<211> LENGTH: 1177
<212> TYPE: PRT
<213> ORGANISM: Artificial sequence
<220> FEATURE:
<223> OTHER INFORMATION: synthetic

<400> SEQUENCE: 12

Met Asp Asn Asn Pro Asn Ile Asn Glu Cys Ile Pro Tyr Asn Cys Leu
1               5                   10                  15

Ser Asn Pro Glu Val Glu Val Leu Gly Gly Glu Arg Ile Glu Thr Gly
            20                  25                  30

```
Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
 50                  55                  60

Trp Gly Ile Phe Gly Pro Ser Gln Trp Asp Ala Phe Leu Val Gln Ile
 65                  70                  75                  80

Glu Gln Leu Ile Asn Gln Arg Ile Glu Glu Phe Ala Arg Asn Gln Ala
                 85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
            130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp His Ala Val
            195                 200                 205

Arg Trp Tyr Asn Thr Gly Leu Glu Arg Val Trp Gly Pro Asp Ser Arg
            210                 215                 220

Asp Trp Ile Arg Tyr Asn Gln Phe Arg Arg Glu Leu Thr Leu Thr Val
225                 230                 235                 240

Leu Asp Ile Val Ser Leu Phe Pro Asn Tyr Asp Ser Arg Thr Tyr Pro
                245                 250                 255

Ile Arg Thr Val Ser Gln Leu Thr Arg Glu Ile Tyr Thr Asn Pro Val
            260                 265                 270

Leu Glu Asn Phe Asp Gly Ser Phe Arg Gly Ser Ala Gln Gly Ile Glu
            275                 280                 285

Gly Ser Ile Arg Ser Pro His Leu Met Asp Ile Leu Asn Ser Ile Thr
290                 295                 300

Ile Tyr Thr Asp Ala His Arg Gly Glu Tyr Tyr Trp Ser Gly His Gln
305                 310                 315                 320

Ile Met Ala Ser Pro Val Gly Tyr Ser Gly Pro Glu Phe Thr Phe Pro
                325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
370                 375                 380

Gly Thr Glu Phe Ala Tyr Gly Thr Ser Ser Asn Leu Pro Ser Ala Val
385                 390                 395                 400

Tyr Arg Lys Ile Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430

Val Ser Met Phe Arg Ser Gly Phe Ser Asn Ser Ser Val Ser Ile Ile
            435                 440                 445
```

-continued

```
Arg Ala Pro Met Phe Ser Trp Ile His Arg Ser Ala Gly Phe Cys Asn
450                 455                 460

Ile Ile Arg Gly Asp Ser Ile Thr Gln Ile Pro Leu Val Lys Ala Tyr
465                 470                 475                 480

Ala Leu His Ser Gly Thr Thr Val Val Arg Gly Pro Gly Phe Thr Gly
                485                 490                 495

Gly Asp Ile Leu Arg Arg Thr Ser Gly Gly Pro Phe Ala Cys Thr Ile
                500                 505                 510

Val Asn Ile Asn Gly Gln Leu Pro Gln Arg Tyr Cys Ala Arg Ile Arg
                515                 520                 525

Tyr Ala Ser Thr Thr Asn Leu Arg Ile Tyr Val Thr Val Ala Gly Glu
530                 535                 540

Arg Ile Phe Ala Gly Gln Phe Asn Lys Thr Met Asn Thr Gly Asp Pro
545                 550                 555                 560

Leu Thr Phe Gln Ser Phe Ser Tyr Ala Thr Ile Asn Thr Ala Phe Thr
                565                 570                 575

Phe Pro Met Arg Gln Ser Ser Phe Thr Val Gly Ala Asp Thr Phe Ser
                580                 585                 590

Ser Gly Asn Glu Val Tyr Ile Asp Arg Phe Glu Leu Ile Pro Val Ala
                595                 600                 605

Ala Thr Leu Gln Ala Glu Tyr Asp Leu Glu Arg Ala Gln Lys Ala Val
                610                 615                 620

Asn Ala Leu Phe Thr Ser Thr Asn Gln Leu Gly Leu Lys Thr Asn Val
625                 630                 635                 640

Thr Asp Tyr His Ile Asp Gln Val Ser Asn Leu Val Thr Tyr Leu Ser
                645                 650                 655

Asp Glu Phe Cys Leu Asp Glu Lys Arg Glu Leu Ser Glu Lys Val Lys
                660                 665                 670

His Ala Lys Arg Leu Ser Asp Glu Arg Asn Leu Leu Gln Asp Ser Asn
                675                 680                 685

Phe Lys Asp Ile Asn Arg Gln Pro Glu Arg Gly Trp Gly Gly Ser Thr
690                 695                 700

Gly Ile Thr Ile Gln Gly Gly Asp Asp Val Phe Lys Glu Asn Tyr Val
705                 710                 715                 720

Thr Leu Ser Gly Thr Phe Asp Glu Cys Tyr Pro Thr Tyr Leu Tyr Gln
                725                 730                 735

Lys Ile Asp Glu Ser Lys Leu Lys Ala Phe Thr Arg Tyr Gln Leu Arg
                740                 745                 750

Gly Tyr Ile Glu Asp Ser Gln Asp Leu Glu Ile Tyr Ser Ile Arg Tyr
                755                 760                 765

Asn Ala Lys His Glu Thr Val Asn Val Pro Gly Thr Gly Ser Leu Trp
                770                 775                 780

Pro Leu Ser Ala Gln Ser Pro Ile Gly Lys Cys Gly Glu Pro Asn Arg
785                 790                 795                 800

Cys Ala Pro His Leu Glu Trp Asn Pro Asp Leu Asp Cys Ser Cys Arg
                805                 810                 815

Asp Gly Glu Lys Cys Ala His His Ser His His Phe Ser Leu Asp Ile
                820                 825                 830

Asp Val Gly Cys Thr Asp Leu Asn Glu Asp Leu Gly Val Trp Val Ile
                835                 840                 845

Phe Lys Ile Lys Thr Gln Asp Gly His Ala Arg Leu Gly Asn Leu Glu
850                 855                 860
```

```
Phe Leu Glu Glu Lys Pro Leu Val Gly Glu Ala Leu Ala Arg Val Lys
865                 870                 875                 880

Arg Ala Glu Lys Lys Trp Arg Asp Lys Arg Glu Lys Leu Glu Trp Glu
                885                 890                 895

Thr Asn Ile Val Tyr Lys Glu Ala Lys Glu Ser Val Asp Ala Leu Phe
            900                 905                 910

Val Asn Ser Gln Tyr Asp Gln Leu Gln Ala Asp Thr Asn Ile Ala Met
        915                 920                 925

Ile His Ala Ala Asp Lys Arg Val His Ser Ile Arg Glu Ala Tyr Leu
    930                 935                 940

Pro Glu Leu Ser Val Ile Pro Gly Val Asn Ala Ala Ile Phe Glu Glu
945                 950                 955                 960

Leu Glu Gly Arg Ile Phe Thr Ala Phe Ser Leu Tyr Asp Ala Arg Asn
                965                 970                 975

Val Ile Lys Asn Gly Asp Phe Asn Asn Gly Leu Ser Cys Trp Asn Val
            980                 985                 990

Lys Gly His Val Asp Val Glu Glu Gln Asn Asn Gln Arg Ser Val Leu
        995                 1000                1005

Val Val Pro Glu Trp Glu Ala Glu Val Ser Gln Glu Val Arg Val
    1010                1015                1020

Cys Pro Gly Arg Gly Tyr Ile Leu Arg Val Thr Ala Tyr Lys Glu
1025                1030                1035

Gly Tyr Gly Glu Gly Cys Val Thr Ile His Glu Ile Glu Asn Asn
    1040                1045                1050

Thr Asp Glu Leu Lys Phe Ser Asn Cys Val Glu Glu Ile Tyr
    1055                1060                1065

Pro Asn Asn Thr Val Thr Cys Asn Asp Tyr Thr Val Asn Gln Glu
    1070                1075                1080

Glu Tyr Gly Gly Ala Tyr Thr Ser Arg Asn Arg Gly Tyr Asn Glu
    1085                1090                1095

Ala Pro Ser Val Pro Ala Asp Tyr Ala Ser Val Tyr Glu Glu Lys
1100                1105                1110

Ser Tyr Thr Asp Gly Arg Arg Glu Asn Pro Cys Glu Phe Asn Arg
1115                1120                1125

Gly Tyr Arg Asp Tyr Thr Pro Leu Pro Val Gly Tyr Val Thr Lys
    1130                1135                1140

Glu Leu Glu Tyr Phe Pro Glu Thr Asp Lys Val Trp Ile Glu Ile
    1145                1150                1155

Gly Glu Thr Glu Gly Thr Phe Ile Val Asp Ser Val Glu Leu Leu
    1160                1165                1170

Leu Met Glu Glu
    1175

<210> SEQ ID NO 13
<211> LENGTH: 1743
<212> TYPE: PRT
<213> ORGANISM: Artificial sequence
<220> FEATURE:
<223> OTHER INFORMATION: synthetic

<400> SEQUENCE: 13

Met Glu Val Asp Val Arg Ile Thr Thr Ala Ala Leu Leu Ile Phe Ala
1               5                   10                  15

Ala Thr Leu Val Ser Ala Gln Thr Asn Gln Leu Arg Cys Thr Tyr Ile
            20                  25                  30
```

```
Gln Glu Ile Pro Arg Gly Asp Thr Pro Val Phe Asn Phe Pro Ser Phe
            35                  40                  45

Asp Gly Val Pro Trp Ser Gln Gln Pro Leu Leu Pro Leu Pro Gln Arg
    50                  55                  60

Glu Glu Leu Cys Met Glu Asp Pro Val Ser Ala Gly Ser Ser Val Ile
65                  70                  75                  80

Met Thr Ile Tyr Met Glu Glu Ile Glu Glu Ile Ala Ile Ala
                85                  90                  95

Lys Leu Asn Tyr Lys Gly Thr Gly Thr Pro Glu Ile Gly Pro Ala Phe
                100                 105                 110

Thr Thr Gly Ser Phe His Thr Leu Gly Pro Val Phe Arg Arg Ile Pro
                115                 120                 125

Glu Asp Gly Glu Trp His Leu Val Ile Thr Asn Lys Gln Asp Phe Glu
            130                 135                 140

Ala Pro Asn Met Gln Arg Tyr Trp Phe Asp Ile Ser Val Pro Gly Glu
145                 150                 155                 160

Ser Val Gly Leu Met Val Leu Leu Glu Ile Val Asn Ile Asp Asp Asn
                165                 170                 175

Ala Pro Ile Val His Met Ile Asp Arg Cys Glu Ile Pro Glu Pro Gly
                180                 185                 190

Thr His Gly Arg Thr Ala Cys Ala Tyr Thr Val Ser Asp Ala Asp Gly
            195                 200                 205

Arg Ile Ser Thr Glu Phe Met Thr Tyr Lys Ile Asp Ser Asp Arg Asn
            210                 215                 220

Asp Gln Asp Phe Phe Glu Leu Val Asn Asp His Thr Met Asp Ala Asp
225                 230                 235                 240

Glu Lys Ile Thr His Met Val Leu Tyr Leu His Lys Asp Leu Asp Phe
                245                 250                 255

Glu Val Asn Pro Leu His Ile Phe Ser Val Thr Ala Phe Asp Ser Lys
                260                 265                 270

Pro Asn Glu His Glu Val Thr Met Met Val Gln Val Gln Asn Thr Asp
            275                 280                 285

Arg Arg Asn Pro Arg Trp Leu Asp Ile Phe Ala Val Gln Gln Phe Asn
290                 295                 300

Glu Lys Gln Ala Lys Ser Phe Thr Val Arg Ala Ile Asp Gly Asp Thr
305                 310                 315                 320

Gly Ile Asn Lys Pro Ile Phe Tyr Arg Ile Glu Thr Glu Asp Glu Asp
                325                 330                 335

Lys Glu Phe Phe Ser Ile Glu Asn Met Gly Glu Gly Arg Asp Gly Ala
                340                 345                 350

Arg Phe His Val Ala Pro Ile Asp Arg Asp Tyr Leu Lys Arg Asp Met
            355                 360                 365

Phe His Ile Arg Ile Ala Tyr Lys Gln Gly Asp Asn Asp Lys Glu
370                 375                 380

Gly Glu Ser Ser Phe Glu Thr Ser Ala Asn Val Thr Ile Ile Ile Asn
385                 390                 395                 400

Asp Ile Asn Asp Gln Arg Pro Glu Pro Phe His Lys Glu Tyr Thr Ile
                405                 410                 415

Ser Ile Met Glu Glu Thr Ala Met Thr Leu Asp Leu Gln Glu Phe Gly
                420                 425                 430

Phe His Asp Arg Asp Ile Gly Pro His Ala Gln Tyr Asp Val His Leu
            435                 440                 445
```

```
Glu Ser Ile Gln Pro Asp Gly Ala His Thr Ala Phe Tyr Ile Ala Pro
        450                 455                 460

Glu Glu Gly Tyr Gln Ala Gln Ser Phe Thr Ile Gly Thr Arg Ile His
465                 470                 475                 480

Asn Met Leu Asp Tyr Glu Asp Asp Tyr Arg Pro Gly Ile Lys Leu
                485                 490                 495

Lys Ala Val Ala Ile Asp Arg His Asp Asn Asn His Ile Gly Glu Ala
            500                 505                 510

Ile Ile Asn Ile Asn Leu Ile Asn Trp Asn Asp Glu Leu Pro Ile Phe
            515                 520                 525

Asp Glu Asp Ala Tyr Asn Val Thr Phe Glu Glu Thr Val Gly Asp Gly
530                 535                 540

Phe His Val Gly Lys Tyr Arg Ala Lys Asp Arg Asp Ile Gly Asp Ile
545                 550                 555                 560

Val Glu His Ser Ile Leu Gly Asn Ala Ala Asn Phe Leu Arg Ile Asp
                565                 570                 575

Ile Glu Thr Gly Asp Val Tyr Val Ser Arg Asp Asp Tyr Phe Asp Tyr
            580                 585                 590

Gln Arg Gln Asn Glu Ile Ile Val Gln Ile Leu Ala Val Asp Thr Leu
        595                 600                 605

Gly Leu Pro Gln Asn Arg Ala Thr Thr Gln Leu Thr Ile Phe Leu Glu
610                 615                 620

Asp Ile Asn Asn Thr Pro Pro Ile Leu Arg Leu Pro Arg Ser Ser Pro
625                 630                 635                 640

Ser Val Glu Glu Asn Val Glu Val Gly His Pro Ile Thr Glu Gly Leu
                645                 650                 655

Thr Ala Thr Asp Pro Asp Thr Thr Ala Asp Leu His Phe Glu Ile Asp
            660                 665                 670

Trp Asp Asn Ser Tyr Ala Thr Lys Gln Gly Thr Asn Gly Pro Asn Thr
        675                 680                 685

Ala Asp Tyr His Gly Cys Val Glu Ile Leu Thr Val Tyr Pro Asp Pro
690                 695                 700

His Asn Arg Gly Arg Ala Glu Gly His Leu Val Ala Arg Glu Val Ser
705                 710                 715                 720

Asp Gly Val Thr Ile Asp Tyr Glu Lys Phe Glu Val Leu Tyr Leu Val
                725                 730                 735

Val Arg Val Ile Asp Arg Asn Thr Val Ile Gly Pro Tyr Asp Glu
            740                 745                 750

Ala Met Leu Thr Val Thr Ile Ile Asp Met Asn Asp Asn Trp Pro Ile
            755                 760                 765

Trp Ala Asp Asn Thr Leu Gln Gln Thr Leu Arg Val Arg Glu Met Ala
        770                 775                 780

Asp Glu Gly Val Ile Val Gly Thr Leu Leu Ala Thr Asp Leu Asp Gly
785                 790                 795                 800

Pro Leu Tyr Asn Arg Val Arg Tyr Thr Met Val Pro Ile Lys Asp Thr
                805                 810                 815

Pro Asp Asp Leu Ile Ala Ile Asn Tyr Val Thr Gly Gln Leu Thr Val
            820                 825                 830

Asn Lys Gly Gln Ala Ile Asp Ala Asp Pro Pro Arg Phe Tyr Leu
        835                 840                 845

Tyr Tyr Lys Val Thr Ala Ser Asp Lys Cys Ser Leu Asp Glu Phe Phe
850                 855                 860
```

-continued

```
Pro Val Cys Pro Pro Asp Pro Thr Tyr Trp Asn Thr Glu Gly Glu Ile
865                 870                 875                 880

Ala Ile Ala Ile Thr Asp Thr Asn Asn Lys Ile Pro Arg Ala Glu Thr
                885                 890                 895

Asp Met Phe Pro Ser Glu Glu Arg Ile Tyr Glu Asn Ala Pro Asn Gly
            900                 905                 910

Thr Lys Ile Thr Thr Ile Ile Ala Ser Asp Gln Asp Arg Asp Arg Pro
        915                 920                 925

Asn Asn Ala Leu Thr Tyr Arg Ile Asn Tyr Ala Phe Asn His Arg Leu
930                 935                 940

Glu Asn Phe Phe Ala Val Asp Pro Asp Thr Gly Glu Leu Phe Val His
945                 950                 955                 960

Phe Thr Thr Ser Glu Val Leu Asp Arg Asp Gly Glu Pro Glu His
                965                 970                 975

Arg Ile Ile Phe Thr Ile Val Asp Asn Leu Glu Gly Ala Gly Asp Gly
                980                 985                 990

Asn Gln Asn Thr Ile Ser Thr Glu Val Arg Val Ile Leu Leu Asp Ile
                995                 1000                1005

Asn Asp Asn Lys Pro Glu Leu Pro Ile Pro Asp Gly Glu Phe Trp
1010                1015                1020

Thr Val Ser Glu Gly Glu Val Glu Gly Lys Arg Ile Pro Pro Glu
1025                1030                1035

Ile His Ala His Asp Arg Asp Glu Pro Phe Asn Asp Asn Ser Arg
1040                1045                1050

Val Gly Tyr Glu Ile Arg Ser Ile Lys Leu Ile Asn Arg Asp Ile
1055                1060                1065

Glu Leu Pro Gln Asp Pro Phe Lys Ile Ile Thr Ile Asp Asp Leu
1070                1075                1080

Asp Thr Trp Lys Phe Val Gly Glu Leu Glu Thr Thr Met Asp Leu
1085                1090                1095

Arg Gly Tyr Trp Gly Thr Tyr Asp Val Glu Ile Arg Ala Phe Asp
1100                1105                1110

His Gly Val Pro Met Leu Asp Ser Phe Glu Thr Tyr Gln Leu Thr
1115                1120                1125

Val Arg Pro Tyr Asn Phe His Ser Pro Val Phe Val Phe Pro Thr
1130                1135                1140

Pro Gly Ser Thr Ile Arg Leu Ser Arg Glu Arg Ala Ile Val Asn
1145                1150                1155

Gly Met Leu Ala Leu Ala Asn Ile Ala Ser Gly Glu Phe Leu Asp
1160                1165                1170

Arg Leu Ser Ala Thr Asp Glu Asp Gly Leu His Ala Gly Arg Val
1175                1180                1185

Thr Phe Ser Ile Ala Gly Asn Asp Glu Ala Ala Glu Tyr Phe Asn
1190                1195                1200

Val Leu Asn Asp Gly Asp Asn Ser Ala Met Leu Thr Leu Lys Gln
1205                1210                1215

Ala Leu Pro Ala Gly Val Gln Gln Phe Glu Leu Val Ile Arg Ala
1220                1225                1230

Thr Asp Gly Gly Thr Glu Pro Gly Pro Arg Ser Thr Asp Cys Ser
1235                1240                1245

Val Thr Val Val Phe Val Met Thr Gln Gly Asp Pro Val Phe Asp
1250                1255                1260
```

-continued

```
Asp Asn Ala Ala Ser Val Arg Phe Val Glu Lys Glu Ala Gly Met
    1265                1270                1275

Ser Glu Arg Phe Gln Leu Pro Gln Ala Asp Asp Pro Lys Asn Tyr
    1280                1285                1290

Arg Cys Met Asp Asp Cys His Thr Ile Tyr Tyr Ser Ile Val Asp
    1295                1300                1305

Gly Asn Asp Gly Asp His Phe Ala Val Glu Pro Glu Thr Asn Val
    1310                1315                1320

Ile Tyr Leu Leu Lys Pro Leu Asp Arg Ser Gln Gln Glu Gln Tyr
    1325                1330                1335

Arg Val Val Val Ala Ala Ser Asn Thr Pro Gly Gly Thr Ser Thr
    1340                1345                1350

Leu Ser Ser Ser Leu Leu Thr Val Thr Ile Gly Val Arg Glu Ala
    1355                1360                1365

Asn Pro Arg Pro Ile Phe Glu Ser Glu Phe Tyr Thr Ala Gly Val
    1370                1375                1380

Leu His Thr Asp Ser Ile His Lys Glu Leu Val Tyr Leu Ala Ala
    1385                1390                1395

Lys His Ser Glu Gly Leu Pro Ile Val Tyr Ser Ile Asp Gln Glu
    1400                1405                1410

Thr Met Lys Ile Asp Glu Ser Leu Gln Thr Val Val Glu Asp Ala
    1415                1420                1425

Phe Asp Ile Asn Ser Ala Thr Gly Val Ile Ser Leu Asn Phe Gln
    1430                1435                1440

Pro Thr Ser Val Met His Gly Ser Phe Asp Phe Glu Val Val Ala
    1445                1450                1455

Ser Asp Thr Arg Gly Ala Ser Asp Arg Ala Lys Val Ser Ile Tyr
    1460                1465                1470

Met Ile Ser Thr Arg Val Arg Val Ala Phe Leu Phe Tyr Asn Thr
    1475                1480                1485

Glu Ala Glu Val Asn Glu Arg Arg Asn Phe Ile Ala Gln Thr Phe
    1490                1495                1500

Ala Asn Ala Phe Gly Met Thr Cys Asn Ile Asp Ser Val Leu Pro
    1505                1510                1515

Ala Thr Asp Ala Asn Gly Val Ile Arg Glu Gly Tyr Thr Glu Leu
    1520                1525                1530

Gln Ala His Phe Ile Arg Asp Asp Gln Pro Val Pro Ala Asp Tyr
    1535                1540                1545

Ile Glu Gly Leu Phe Thr Glu Leu Asn Thr Leu Arg Asp Ile Arg
    1550                1555                1560

Glu Val Leu Ser Thr Gln Gln Leu Thr Leu Leu Asp Phe Ala Ala
    1565                1570                1575

Gly Gly Ser Thr Val Leu Pro Gly Gly Glu Tyr Ala Leu Ala Val
    1580                1585                1590

Tyr Ile Leu Ala Gly Ile Ala Ala Leu Leu Ala Val Ile Cys Leu
    1595                1600                1605

Ala Leu Leu Ile Ala Phe Phe Ile Arg Thr Arg Ala Leu Asn Arg
    1610                1615                1620

Arg Leu Glu Ala Leu Ser Met Thr Lys Tyr Gly Ser Val Asp Ser
    1625                1630                1635

Gly Leu Asn Arg Ala Gly Leu Ala Ala Pro Gly Thr Asn Lys His
    1640                1645                1650
```

```
Ala Ile Glu Gly Ser Asn Pro Ile Trp Asn Glu Thr Ile Lys Ala
    1655            1660            1665

Pro Asp Phe Asp Ala Ile Ser Asp Val Ser Asn Asp Ser Asp Leu
    1670            1675            1680

Ile Gly Ile Glu Asp Leu Pro Gln Phe Arg Ser Asp Tyr Phe Pro
    1685            1690            1695

Pro Gly Asp Asp His Ser Leu Gln Gly Ile Val Leu Asp Asn Gln
    1700            1705            1710

Asn Asn Asp Thr Val Ala Thr His Gly Asn Asn Phe Lys Phe Asn
    1715            1720            1725

Ala Ser Pro Phe Ser Pro Glu Phe Gly Asn Thr Pro Ile Arg Arg
    1730            1735            1740
```

MULTI FUNCTIONAL TOXINS

REFERENCE TO RELATED APPLICATION

This application claims the benefit of U.S. Provisional Application No. 62/196,249, filed Jul. 23, 2015, and U.S. Provisional Application No. 62/328,543, filed Apr. 27, 2016, each of which is herein incorporated by reference in its entirety.

INCORPORATION OF SEQUENCE LISTING

The sequence listing that is contained in the file named "MONS395US_sequence_listing.txt", which is 111,500 bytes in size (measured in MS-Windows) and was created on Jul. 20, 2016, is filed herewith by electronic submission and is incorporated herein by reference.

FIELD OF THE INVENTION

The invention generally relates to the field of insect inhibitory proteins. Novel insect inhibitory or pesticidal proteins with altered binding to one or more insect receptor(s), and that exhibit insect inhibitory activity against pests of crop plants, are disclosed. In particular, the disclosed proteins are insecticidally active against agriculturally-relevant pests of crop plants and seeds, particularly Coleopteran, Lepidopteran, and Hemipteran species of insect pests. Plants, plant parts, and seeds containing a recombinant polynucleotide construct encoding one or more of the disclosed toxin proteins are also provided.

BACKGROUND OF THE INVENTION

Many insect-pesticidal proteins exert their pesticidal effects by first binding to a target receptor on or near the surface of a cell within the target insect pest, and then forming a pore in the membrane to which the target pest receptor is on, or is embedded within. Thus, if a target pest becomes resistant to the pesticidal protein, the underlying cause of the resistance that the pest has developed may be a result of a change in the interaction between the pesticidal protein and the target receptor of the insect cell. The binding of a pesticidal protein to a cognate receptor in a target pest, allowing the pesticidal protein to exert its pesticidal effects upon that pest, is considered to be a "mode of action" (MOA). The inability of a pesticidal protein to bind to its cognate receptor may be referred to as a "loss of the mode of action" of that pesticidal protein. The loss of a mode of action typically results in the target pest becoming resistant to that particular pesticidal protein. Such pesticidal proteins are not typically known to exhibit the ability to bind to more than one receptor in the target pest.

An important goal in the field of Agricultural Biotechnology as it relates to insect pest control is to avoid or delay the development of resistance to an inhibitory or insecticidal protein in a population of insect pests targeted by a particular pesticidal protein. Providing two or more modes of action in the diet of a target pest can delay or reduce the chance that an insect pest may develop such resistance. Two or more modes of action may be provided as at least two different pesticidal proteins that are both toxic to the same insect species but which each bind to different receptors. This approach has been referred to as the dual mode of action approach. Future products considered by the agriculture industry include developing crop plants with at least two modes of action, provided by two or more different pesticidal proteins each toxic to the same insect species but each providing the pesticidal effect as a result of binding to different receptors.

Thus there is a need in the art to be able to provide as many modes of action for controlling any single crop pest as possible in a single plant genome in order to reduce the likelihood of target pests developing resistance to a single mode of action. The prior art has not taught that multiple modes of action could be provided by a single protein toxin or by a single pesticidal protein which has been engineered to have the ability to bind to different receptors within the same target pest and confer effective pesticide activity upon the target pest.

SUMMARY OF THE INVENTION

In one aspect, the invention provides a method for controlling an infestation by a target pest in a crop, said method comprising: contacting said target pest with a pesticidal protein that binds to a first receptor and a second receptor of the target pest; wherein the first receptor is different from the second receptor; and wherein the binding to the second receptor does not interfere with the binding to the first receptor. In one embodiment of the method, the pesticidal protein is provided within the diet of the target pest. In another embodiment of the method, the pesticidal protein is topically applied to the crop or the target pest. In some embodiments the pesticidal protein does not naturally bind to both the first receptor and the second receptor.

In certain embodiments the pesticidal protein is engineered to enable or improve binding to the first receptor or the second receptor. In some embodiments the pesticidal protein is engineered by a method for protein modification selected from the group consisting of: rational design, structure based design, semi-rational design, directed evolution, phage display, selection of peptides from a peptide library for inclusion in the pesticidal protein for targeting the pesticidal protein to bind to a receptor, operable linkage of the pesticidal protein to an antibody, antibody binding domain, alphabody, lipocalin, anticalin, random mutagenesis, rational design, structure based design, semi-rational design, high throughput optimization focusing on the study of 3D protein toxin models and selecting surface exposed features into which changes can be introduced, and construction of chimeric proteins produced from segments of two or more different proteins.

The invention further provides a method wherein the pesticidal protein is expressed in a plant of the crop in which pest infestation is controlled. Thus, in certain embodiments the pesticidal protein is encoded by a polynucleotide molecule incorporated in the genome of the plant.

Also provided by the invention are embodiments wherein the first receptor or the second receptor is a pest cell surface protein or an insect protein. Contemplated methods may further comprise providing to the target pest a pesticidal agent that is different from the pesticidal protein and is selected from the group consisting of a bacterial toxin, a plant toxin, an arachnid toxin, a venom toxin, and a dsRNA targeting for suppression of an essential gene in said target pest. In certain embodiments the pesticidal agent is selected from the group consisting of Cry1A, Cry1Aa, Cry1Ab, Cry1Ac, Cry1A.105, Cry1B, Cry1Bb1, Cry1C, Cry1Ca, Cry1C amino acid sequence variants, Cry1D, Cry1Da, Cry1D amino acid sequence variants, Cry1E, Cry1F, Cry1Fa, Cry1G, Cry1H, Cry1I, Cry1J, Cry1K, Cry1L, Cry2A, Cry2Aa, Cry2Ab, Cry2Ae, Cry3, Cry3Aa, Cry3A amino acid sequence variants, Cry3B, Cry3Bb, Cry3Bb amino acid sequence variants, Cry4B, Cry5, Cry6, Cry7, Cry8, Cry9, Cry15, Cry34, Cry35, Cry43A, Cry43B, Cry51Aa1, ET29, ET33, ET34, ET35, ET66, ET70, Cry1A.105, TIC400, TIC407, TIC417, TIC431, TIC800, TIC807, TIC834, TIC853, TIC901, TIC1201, TIC1415, TIC3131, VIP3A, VIP3B, 5307, Axmi184, Axmi205, eHIP toxin proteins, insecticidal DIG proteins, venom proteins, and the insecticidal core toxin of each of the foregoing. In some embodiments, a) the pesticidal agent is toxic to the same pest as the pesticidal protein; or b) the pesticidal agent is toxic to a different pest than the pesticidal protein.

In particular embodiments the pesticidal agent is a protein that binds to a third receptor. In some embodiments, the pesticidal agent is engineered to bind to a fourth receptor, and wherein said third receptor and said fourth receptor are different, and binding of said pesticidal agent to said fourth receptor does not interfere with binding to said third receptor.

In certain embodiments the target pest is selected from the group consisting of a Lepidopteran insect, a Coleopteran insect, a Hemipteran insect, a Homopteran insect, a Hymenopteran insect, a Dipteran insect, a nematode, a pathogenic microorganism, a pathogenic fungi, and a pathogenic bacterium. The invention further provides embodiments wherein the crop comprises a monocotyledonous plant or a dicotyledonous plant. In certain embodiments the monocotyledonous plant is selected from the group consisting of rice, wheat, barley, grasses, bentgrass, sugarcane, oats, sorghum, chives, shallots, and corn; or the dicotyledonous plant is selected from the group consisting of cotton, canola, soybean, beans, sugarbeet, alfalfa, vegetables, fruits, curcubits, melons, pigeonpea, peppers, and peanut.

Another aspect of the invention relates to a pesticidal protein that binds to at least a first receptor and a second receptor of a target pest; wherein the first receptor is different from the second receptor; wherein the binding to the second receptor does not interfere with the binding to the first receptor; and wherein the pesticidal protein does not naturally bind to both the first receptor and the second receptor. In some embodiments, the pesticidal protein comprises or displays enhanced pesticidal activity as compared to a pesticidal protein that binds to only one of the first receptor or the second receptor. In certain embodiments the pesticidal protein is encoded by a polynucleotide molecule incorporated in the genome of a plant. In particular embodiments the pesticidal protein is selected from the group consisting of: an insecticidal toxin, a nematicidal protein, a fungicidal protein, or a bacteriocidal protein. Thus in some embodiments the insecticidal toxin is selected from the group consisting of: a Bt toxin, a *Bacillus* species insecticidal toxin other than a Bt toxin, a *Photorhabdus* insecticidal toxin, a *Xenorhabdus* insecticidal toxin, a chimeric toxin, an arachnid insecticidal toxin, and a lectin. In particular embodiments the chimeric toxin comprises a toxin fusion with a partner protein or a toxin protein produced from the fusion of two or more portions of different Bt toxins.

In certain embodiments the target pest is selected from the group consisting of a Lepidopteran insect, a Coleopteran insect, a Hemipteran insect, a Homopteran insect, a Hymenopteran insect, a Dipteran insect, a nematode, a pathogenic microorganism, a pathogenic fungi, and a pathogenic bacterium.

Yet another aspect of the invention relates to a plant or plant cell comprising a pesticidally effective amount of the pesticidal protein that binds to at least a first receptor and a second receptor of a target pest; wherein the first receptor is different from the second receptor; wherein the binding to the second receptor does not interfere with the binding to the first receptor; and wherein the pesticidal protein does not naturally bind to both the first receptor and the second receptor. A seed produced from such a plant, wherein the seed comprises a polynucleotide molecule encoding the pesticidal protein in its genome, is also contemplated.

In certain embodiments, the plant or plant cell of claim 25, further comprises: a) a pesticidal agent toxic to the target pest, wherein the pesticidal agent is different from the pesticidal protein and is selected from the group consisting of a bacterial toxin, a plant toxin, an arachnid toxin, and a dsRNA targeting for suppression an essential gene in said target pest; or b) a pesticidal agent toxic to a different pest, wherein said pesticidal agent is different from said pesticidal protein and is selected from the group consisting of a bacterial toxin, a plant toxin, an arachnid toxin, and a dsRNA targeting for suppression an essential gene in said different pest.

Another aspect of the invention provides a recombinant polynucleotide molecule encoding the pesticidal protein that binds to at least a first receptor and a second receptor of a target pest; wherein the first receptor is different from the second receptor; wherein the binding to the second receptor does not interfere with the binding to the first receptor; and wherein the pesticidal protein does not naturally bind to both the first receptor and the second receptor. A polynucleotide construct comprising the recombinant polynucleotide molecule is also provided.

Further contemplated is a composition comprising the pesticidal protein, formulated for topical application to the target pest or to a crop plant.

Another aspect of the invention provides a method for controlling crop pest infestation by a first target pest and a second target pest different from the first, comprising: providing in the diet of the first and the second target pests a pesticidal protein that binds to a first receptor in the gut of the first target pest and to a second receptor in the gut of the second target pest, wherein said first receptor and second receptor are not the same. In one embodiment of such a method, the pesticidal protein is engineered to enable or improve binding to the first receptor or the second receptor, and wherein the pesticidal protein does not naturally bind to both the first receptor and the second receptor.

Also provided is a method for reducing the number of pesticidal proteins or polynucleotide molecules encoding a pesticidal protein to be included in a crop species for controlling a first target pest and a second target pest different from the first, comprising: providing in the genome of the crop species a polynucleotide molecule encoding a pesticidal protein that binds a first receptor in the first target pest and a second receptor in the second target pest, wherein said first receptor is different from said second receptor.

Thus, in another aspect, there is provided a crop grown in a field, wherein the crop comprises a polynucleotide molecule encoding a pesticidal protein that controls a) a single target pest of said crop, wherein said pesticidal protein is engineered to contain two or more modes of action for controlling said single target pest; or b) a first target pest of said crop by binding to at least one first receptor in said first target pest, and a second target pest of said crop by binding to at least one second receptor in said second target pest, wherein said second receptor is different than the first receptor and said second target pest is different from said first target pest.

BRIEF DESCRIPTION OF THE SEQUENCES

SEQ ID NO:1 is the amino acid sequence of full-length Cry1Ac1 toxin.

SEQ ID NO:2 is the amino acid sequence of PACE-derived Cry1Ac1 toxin variant Protein 3.

SEQ ID NO:3 is the amino acid sequence of PACE-derived Cry1Ac1 toxin variant Protein 4.

SEQ ID NO:4 is the amino acid sequence of PACE-derived Cry1Ac1 toxin variant Protein 5.

SEQ ID NO:5 is the amino acid sequence of TIC2160 toxin.

SEQ ID NO:6 is the amino acid sequence of a *Spodoptera frugiperda* (fall armyworm) cadherin binding peptide: VDWWSPFYDRLK.

SEQ ID NO:7 is the amino acid sequence of TIC2160* toxin variant, comprising the Sf cadherin binding protein of SEQ ID NO:6 inserted into Domain 4 of TIC2160 (SEQ ID NO:5).

SEQ ID NO:8 is the amino acid sequence of full-length TIC105 toxin.

SEQ ID NO:9 is the amino acid sequence of a *Spodoptera frugiperda* (fall armyworm) cadherin binding peptide: SDYGWWRPFQPG.

SEQ ID NO:10 is the amino acid sequence of a TIC105 toxin variant, comprising the Sf cadherin binding protein of SEQ ID NO:9 inserted into the TIC105 scaffold (SEQ ID NO:8).

SEQ ID NO:11 is the amino acid sequence of a Cry1Ac1 toxin variant, comprising the Sf cadherin binding protein of SEQ ID NO:6 inserted into the Cry1Ac1 scaffold (SEQ ID NO:1).

SEQ ID NO:12 is the amino acid sequence of PACE-derived TIC105 toxin variant IS0349 comprising the following mutations to TIC105 (SEQ ID NO:8): F328Y, S404I, E461G, N463C, A467R, S468G, H480Y, T481A, Q483H, Y510C, R524C, D556N, S580R, T608A, E612Q, N616D.

SEQ ID NO:13 is the amino acid sequence of chimeric cadherin derived from *Spodoptera frugiperda* (fall armyworm) cadherin and *Chrysodeixis includens* (soybean looper) cadherin.

DETAILED DESCRIPTION OF THE INVENTION

The present invention provides novel methods for producing multifunctional insect-active pesticidal proteins displaying one or more additional mode(s) of action relative to an unmodified or wild-type pesticidal protein which does not comprise such modification. Such multifunctional proteins are also provided by the invention. In particular, the present methods allow for identification, for instance via directed evolution or any other method known for producing variant polypeptide sequences, of polypeptide sequences which allow for functional interaction (e.g. binding) to a "receptor" protein present in an insect cell. A protein comprising the identified polypeptide sequence responsible for the newly identified binding may then be utilized for enhanced insect control, or for instance, the identified polypeptide sequence conferring novel binding activity may be added to a pre-existing protein, such as an insecticidal toxin which in its native form does not interact with a receptor present in a given insect cell, or on the surface of such insect cell including an insect gut cell, to create a modified protein exhibiting an additional mode of action ("MOA") for insect pest control.

Such addition of polypeptide sequence to result in a broader spectrum of interaction with insect receptor(s) can surprisingly be performed without affecting the functional activity of the modified protein regarding the original receptor with which the corresponding wild-type protein typically interacts. Thus the present invention allows for producing a modified pest control protein with an enhanced spectrum of activity against one or more additional insect pests, relative to the spectrum of activity typically seen for the corresponding (i.e. "scaffold") wild-type pesticidal protein. Such a modified protein may not only exhibit a novel spectrum of insecticidal activity, but may also be useful for delaying, or reducing the likelihood of, development of resistance to a given insect control protein in an insect population.

Pesticidal proteins that are delivered in the diet of a pest generally exert their pesticidal effects by first binding to a target pest receptor on or near the surface of a cell within the target pest, resulting in formation of a pore in the membrane to which the target pest receptor is on, or is embedded within. Pore formation causes cell membrane damage; the pest typically ceases eating, becomes dehydrated, and/or stunted and subsequently dies. The step of binding is critical and, for any particular pest being targeted for control by the pesticidal protein, binding occurs to only one particular receptor which is generally a protein that is produced by the target pest and is surface exposed, i.e., exposed on the surface of the gut membrane that is exposed to the biological materials consumed as food by the pest and which pass through the insect alimentary canal, the gut of the pest.

It is generally recognized that such pesticidal proteins are not known to exhibit the ability to bind to more than one receptor in the target pest. Thus in the event that the target pest evolves to become resistant to a pesticidal protein, the underlying cause of the resistance that the pest has developed may be a result of loss of expression of the target receptor to which the pesticidal protein binds; alternatively some feature of the target receptor may have changed, resulting in the loss of recognition for binding by the previously active pesticidal protein. It is also generally recognized that the first receptor to which a pesticidal protein binds in a first target pest and exerting some biological effect upon such first target pest analogous to controlling the first target pest, is also a receptor that exhibits a binding epitope that is substantially similar if not the same as a binding epitope on a second receptor in a second target pest that is also capable of being controlled by the same pesticidal protein. For example, a toxin protein that controls a corn earworm and also controls a pink bollworm is generally recognized as targeting for binding the same or a similar epitope.

By reference to control, controlling, or controlled, with reference to pest control, insect control, nematode control, and the like, it is intended to mean the feature of stunting, mortality, cessation of feeding, repulsion, or absence of damage to a particular crop or plant tissue (such as flower, stem, leaf, seed, fruit, and root) and the like, a property that can be observed by those of ordinary skill in the art.

The binding of a pesticidal protein to a single receptor in a target pest so that the pesticidal protein can exert its pesticidal effects upon that pest is considered to be a mode of action (MOA). Loss of the pesticidal proteins' ability to exert its pesticidal effects upon the target pest because of the inability of the pesticidal protein to bind to its cognate receptor is referred to as a loss of the mode of action of that pesticidal protein. The loss of a mode of action results in the target pest becoming resistant to that particular pesticidal protein.

An effective mechanism to avoid the development of resistance of a population of pests targeted by a particular pesticidal protein is to provide in the diet of the target pest two or more modes of action for pest control. Typically in the art, as an approach for providing two or more modes of action, at least two different pesticidal proteins may be provided, that are both toxic to the same insect species but which each bind to different receptors. In controlling insect pests in crop fields, this approach has been referred to as the dual mode of action approach, and when *Bacillus thuringiensis* protein toxins are used to convey these modes of action in transgenic plants expressing such toxin proteins, the plant product may be characterized as a plant conveying "dual Bt's" or "dual modes of action."

It may be advantageous to include in engineered crop plants at least two modes of action by providing two or more different pesticidal proteins each toxic to the same insect species, but each providing their pesticidal effect as a result of binding to a different receptor present in a target insect pest. However, the ability to stack sequences for plant expression, whether in a single vector that is introduced into the transgenic plant, or in multiple vectors that are also introduced into the genome of the plant but in different places in the plant genome, is becoming increasingly difficult, even though mechanisms for site directed integration or gene editing are being developed for use in many of the principle crops in cultivation today. Thus there is a need in the art to be able to provide as many modes of action for controlling any single crop pest as possible on or in a single plant, and within the plant genome, in order to reduce the likelihood of development of resistance of any single target pest to any one of these several (multiple) modes of action. No prior art has taught that the multiple modes of action could be provided by a single pesticidal agent, whether the pesticidal agent is a chemical agent or a protein toxin. No prior art has taught or disclosed the providing of a single pesticidal protein into which the ability to bind to different receptors within the same target pest has been engineered (i.e., incorporated) and to confer effective pesticide activity upon the target pest regardless of the receptor that is bound by the pesticidal protein. No prior art has taught or disclosed that in any such protein, the binding of one receptor by the pesticidal protein does not diminish or reduce the ability of the pesticidal protein to bind to any other receptor, and vice versa.

The present invention thus provides approaches for controlling pests in the field that have previously developed resistance to a particular field exposed toxin. For example, a Cry1Ac resistant cabbage looper that was previously sensitive to Cry1Ac can now be controlled by introducing into a plant a Cry1Ac amino acid sequence variant that exerts its effects upon cabbage looper by binding to an additional or two or more different receptors exposed on the surface of the cells in the gut of cabbage looper larvae. In the event that one of these receptors is not present or is no longer present in a given target insect population, the other receptor can function to allow for Cry1A binding and to introduce a pore into the gut of the looper, causing insect morbidity and mortality, thus controlling the pest.

While the described features of the invention are generally applicable to any protein toxin and the disclosure herein primarily relates to Bt toxins, one of ordinary skill in the art will recognize that these principles are generally applicable across all fields of toxin science. The present invention is generally applicable to any toxin or pesticidal protein including but not limited to Cry1A, Cry1Aa, Cry1Ab, Cry1Ac, Cry1A.105, Cry1B, Cry1Bb1, Cry1C, Cry1Ca, Cry1C amino acid sequence variants, Cry1D, Cry1Da, Cry1D amino acid sequence variants, Cry1E, Cry1F, Cry1Fa, Cry1Fa truncated protein toxins or amino acid sequence variants, Cry1G, Cry1H, Cry1I, Cry1J, Cry1K, Cry1L, Cry2A, Cry2Aa, Cry2Ab, Cry2Ae, Cry3, Cry3Aa, Cry3A amino acid sequence variants, Cry3B, Cry3Bb, Cry3Bb amino acid sequence variants, Cry4B, Cry5, Cry6, Cry7, Cry8, Cry9, Cry15, Cry34, Cry35, Cry43A, Cry43B, Cry51Aa1, ET29, ET33, ET34, ET35, ET66, ET70, Cry1A.105, TIC400, TIC407, TIC417, TIC431, TIC800, TIC807, TIC834, TIC853, TIC901, TIC1201, TIC1415, TIC3131, VIP3A, VIP3B, 5307, Axmi184, Axmi205, eHIP toxin proteins, insecticidal DIG proteins, venom proteins, and including the insecticidal core toxin of each of the foregoing.

In some aspects, this disclosure provides variant Bt toxins that are derived from a wild-type Bt toxin and have at least one variation in the amino acid sequence of the protein as compared to the amino acid sequence present within a cognate wild-type Bt toxin or at least one variation in the encoding nucleic acid sequence that results in a change in a codon that results in an amino acid change in the amino acid sequence present within a cognate wild type Bt toxin. The variation in amino acid sequence generally results from a mutation, insertion, or deletion in a DNA coding sequence. Mutation of a DNA sequence can result in a nonsense mutation (e.g., a transcription termination codon (TAA, TAG, or TAA, i.e. amber, ocher, and opal mutations) that produces a truncated protein), a missense mutation (e.g., an insertion or deletion mutation that shifts the reading frame of the coding sequence), or a silent mutation (e.g., a change in the coding sequence that results in a codon that codes for the same amino acid normally present in the cognate protein, i.e., a synonymous mutation, or introduces an amino acid substitution which does not alter the cognate proteins' functionality). In some embodiments, mutation of a DNA sequence results in a non-synonymous (i.e., conservative, semi-conservative, or radical) amino acid substitution.

It has been discovered as described herein that pesticidal proteins can be amended, modified, or altered to exhibit two or more modes of action as a result of causing the pesticidal protein to bind to more than one receptor in any particular target pest intended for control by using the pesticidal protein.

By reference to amended, modified or altered, it is intended that a particular amino acid sequence of a particular pesticidal protein be changed in any number of ways known in the art to achieve the properties intended as set forth in this application. For example, a protein's amino acid sequence can be amended, modified, or altered by engineering into such protein amino acid sequence certain changes that are result effective in achieving the properties described herein. The skilled artisan can insert additional (i.e., supplemental) amino acids to add to the native amino acid sequence, for example by introducing peptides of various lengths (from two or more consecutive amino acids up to several dozen consecutive amino acids, but more preferably from about five consecutive amino acids to any length of amino acids from five to about fifty consecutive amino acids, i.e., a peptide of such length of amino acids).

Surprisingly, it is found that an additional epitope may be introduced into a pesticidal protein such as a Bt protein, that allows for its binding to a receptor that is different from the normal cognate receptor to which the pesticidal protein binds in the ordinary course, and without significantly changing the normal receptor binding epitope nor changing the toxic properties typically conferred by such pesticidal protein when it binds to the normal receptor in a particular target pest. Changes to a pesticidal protein may also include deletion of consecutive amino acids to introduce new binding epitopes without modifying the ordinary normal cognate receptor binding epitope, and changing various amino acids within the amino acid sequence of the pesticidal protein in order to cause the pesticidal protein to bind supplemental epitopes/receptors without changing the pesticidal proteins' normal cognate receptor binding capability and without changing the pesticidal proteins' normal pesticidal capabilities. In addition, reference to amended, modified and altered and methods for introducing such changes into a proteins' amino acid sequence can include de novo engineering of a nucleotide sequence to reflect the changed amino acid sequence, constructing a novel amino acid sequence to encode such altered, amended or modified amino acid sequence, or evolving a nucleotide sequence to reflect the changes to be introduced into such pesticidal protein amino acid sequence. All such methods for introducing such changes result in varying the amino acid sequence to introduce supplemental amino acids, whether single changes at specific amino acid positions normally within the naturally occurring amino acid sequence (i.e., substitutions of one amino acid for another, whether conserved changes or non-conserved changes) or introducing or deleting/removing consecutive amino acids (peptides) within the pesticidal protein amino acid sequence.

Wild-type Bt toxins are encoded by genes of the cry gene family, e.g., by the Cry1Ac gene. The amount or level of variation between a wild-type Bt toxin and a variant Bt toxin provided herein can be expressed as the percent identity of the nucleic acid sequences or amino acid sequences between the two genes or proteins. In some embodiments, the amount of variation is expressed as the percent identity at the amino acid sequence level.

The amount or level of variation between a wild-type Bt toxin and a variant Bt toxin can also be expressed as the number of mutations present in the amino acid sequence encoding the variant Bt toxin relative to the amino acid sequence encoding the wild-type Bt toxin. In some embodiments, an amino acid sequence encoding a variant Bt toxin comprises between about 1 mutation and about 100 mutations, about 10 mutations and about 90 mutations, about 20 mutations and about 80 mutations, about 30 mutations and about 70 mutations, or about 40 and about 60 mutations relative to an amino acid sequence encoding a wild-type Bt toxin. In some embodiments, an amino acid sequence encoding a variant Bt toxin comprises more than 100 mutations relative to an amino acid sequence encoding a wild-type Bt toxin.

The location of mutations in an amino acid sequence encoding a variant Bt toxin are also contemplated by the disclosure. Generally, mutations may occur in any portion (e.g., N-terminal, interior, or C-terminal) of an amino acid sequence. Mutations may also occur in any functional domain (e.g., the pore-forming domain, the receptor-binding domain, or the sugar-binding domain). In some embodiments, at least one mutation is located in the receptor-binding domain of the Bt variant toxin (i.e., that portion of the Bt variant toxin that interacts with the TBR).

In some aspects, the disclosure relates to variant Bt toxins that bind to receptors in Bt toxin-resistant pests with higher affinity than the wild-type Bt toxin from which they are derived (e.g., Cry1Ac, represented by SEQ ID NO: 1). Generally, binding of a Bt toxin to a receptor is mediated by the interaction between the receptor binding domain (e.g., target binding region) of the Bt toxin and the cell surface receptor of the target cell. Thus, in some embodiments the disclosure provides a protein comprising a receptor binding domain, wherein the receptor binding domain comprises an amino acid sequence that is at least 70%, at least 75%, at least 80%, at least 85%, at least 90%, at least 95%, or at least 99% identical to SEQ ID NO: 1, wherein the receptor binding domain comprises at least one mutation.

This disclosure relates, in part, to the discovery that pesticidal proteins can be engineered to bind more than one receptor, particularly to bind a receptor that the pesticidal protein would not ordinarily bind to in nature. Such methods include but are not limited to protein modification methods such as rational design, structure based design, semi-rational design, directed evolution (including but not limited to shuffling methods for evolving coding sequences to produce modified or variant amino acid sequences, phage assisted evolution for evolving coding sequences to produce modified or variant amino acid sequences, and the like), phage display methods for selecting modified peptides capable of binding particular target moiety/epitope, selection of peptides from a peptide library that are capable of binding a particular target moiety/epitope for inclusion in the pesticidal protein for targeting the pesticidal protein to bind to a receptor to which the pesticidal protein lacking the peptide would have no binding affinity, operable linkage of the pesticidal protein to an antibody, operable linkage of the pesticidal protein to an antibody binding domain, operable linkage of the pesticidal protein to an alphabody, operable linkage of the pesticidal protein to an lipocalin, operable linkage of the pesticidal protein to an anticalin, random mutagenesis to obtain an amino acid sequence variant capable of binding a second receptor, rational design of denovo amino acid sequences capable of binding to a first receptor and to a second receptor that is different from the first, structure based design of denovo amino acid sequences capable of binding to a first receptor and to a second receptor that is different from the first, semi-rational design of denovo amino acid sequences capable of binding to a first receptor and to a second receptor that is different from the first, for example high through put optimization focusing on the study of 3D protein models of a cognate toxin and selecting surface exposed features into which changes (such as amino acid sequence changes, or inclusion or deletion of peptide segments) can be introduced.

Also, chimeragenesis to achieve the features taught here is included as a method for producing a protein that exhibits more than one mode of action when used in a particular target pest. A chimeric protein may bind to one or more receptors that are different from each other compared to the receptors that to which the underlying non-chimeric toxins from which the chimeric protein was constructed bind. For example, a chimeric toxin produced from a Cry1Ab and a Cry1Fa may provide for binding to more than one receptor in a particular targeted pest.

Such methods are useful for producing variant Bt toxins (or other pesticidal proteins) that have altered binding capabilities. In some embodiments, a variant Bt toxin binds to a toxin binding region of a cell surface receptor with higher affinity than the cognate Bt toxin. Several cell surface receptors are known in the art. Examples of cell surface receptors include, but are not limited to, cadherin-like proteins (CADR), glycosylphosphatidyl-inositol (GPI)-anchored aminopeptidase-N (APN), and GPI-anchored alkaline phosphatase (ALP), however, Cry1Ac does not bind to, or recognize, each of these as a target receptor. A variant Bt toxin that binds with higher affinity can have an increase in binding strength ranging from about 2-fold to about 100-fold or greater, about 5-fold to about 50-fold, or about 10-fold to about 40-fold, relative to the binding strength of the wild-type Bt toxin from which the variant Bt toxin was derived. Binding strength can be measured or determined using any suitable method known in the art, for example by determining the dissociation constant (Kd) of an interaction. The skilled artisan will generally understand the metes and bounds of these methods.

In some aspects, the disclosure relates to the surprising discovery that toxins that bind to more than two different receptors in a particular target pest are effective in killing pests with greater efficacy and are more durable. In addition, such engineered toxins are capable of restoring the ability to control a pest that has become refractory or resistant to treatment with the wild-type Bt toxin from which the variant Bt toxins are derived.

Variant Bt toxins described by the disclosure may be effective against a wide variety of pests, for example insects. In some embodiments, the insects are selected from the group consisting of the insect Orders Lepidoptera, Coleoptera, Hemiptera, and Diptera, including adults, pupae, larvae and neonates.

Insects of the order Lepidoptera include, but are not limited to, armyworms, cutworms, loopers, and heliothines in the Family Noctuidae, e.g., fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae, e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae, e.g., codling moth (*Cydia pomonella*), grape berry moth (*Endopiza viteana*), oriental fruit moth (*Grapholita molesta*), sunflower bud moth (*Suleima helianthana*); and many other economically important Lepidoptera, e.g., diamondback moth (*Plutella xylostella*), pink bollworm (*Pectinophora gossypiella*) and gypsy moth (*Lymantria dispar*). Other insect pests of order Lepidoptera include, e.g., *Alabama argillacea* (cotton leaf worm), *Archips argyrospila* (fruit tree leaf roller), *Archips rosana* (European leafroller) and other *Archips* species, *Chilo suppressalis* (Asiatic rice borer, or rice stem borer), *Cnaphalocrocis medinalis* (rice leaf roller), *Crambus caliginosellus* (corn root webworm), *Crambus teterrellus* (bluegrass webworm), *Diatraea grandiosella* (southwestern corn borer), *Diatraea saccharalis* (surgarcane borer), *Earias insulana* (spiny bollworm), *Earias vittella* (spotted bollworm), *Helicoverpa armigera* (American bollworm), *Helicoverpa zea* (corn earworm or cotton bollworm), *Heliothis virescens* (tobacco budworm), *Herpetogramma licarsisalis* (sod webworm), *Lobesia botrana* (European grape vine moth), *Phyllocnistis citrella* (citrus leafminer), *Pieris brassicae* (large white butterfly), *Pieris rapae* (imported cabbageworm, or small white butterfly), *Plutella xylostella* (diamondback moth), *Spodoptera exigua* (beet armyworm), *Spodoptera litura* (tobacco cutworm, cluster caterpillar), and *Tuta absoluta* (tomato leafminer). Other examples of Lepidoptera include *Zeuzera coffeae, Hyalarcta* spp., *Eumeta* spp., *Manduca sexta, Manduca quinquemaculata, Peridroma saucia, Colias eurytheme, Plathypena scabra, Trichoplusia ni, Evergestos ro, Evergestos psa, Evergestos os*, and *Pthorimaea operculella.*

Contemplated insects of the order Coleoptera include, but are not limited to, *Agriotes* spp., *Anthonomus* spp., *Atomaria linearis, Chaetocnema tibialis, Cosmopolites* spp., *Curculio* spp., *Dermestes* spp., *Diabrotica* spp., *Epilachna* spp., *Eremnus* spp., *Leptinotarsa decemlineata, Lissorhoptrus* spp., *Melolontha* spp., *Orycaephilus* spp., *Otiorhynchus* spp., *Phlyctinus* spp., *Popillia* spp., *Psylliodes* spp., *Rhizopertha* spp., *Scarabeidae, Sitophilus* spp., *Sitotroga* spp., *Tenebrio* spp., *Tribolium* spp. and *Trogoderma* spp, particularly when the pest is *Diabrotica virgifera virgifera* (Western Corn Rootworm, WCR), *Diabrotica barberi* (Northern Corn Rootworm, NCR), *Diabrotica virgifera zeae* (Mexican Corn Rootworm, MCR), *Diabrotica balteata* (Brazilian Corn Rootworm (BZR), *Diabrotica undecimpunctata howardii* (Southern Corn Rootworm, SCR) and a Brazilian Corn Rootworm complex (BCR) consisting of *Diabrotica viridula* and *Diabrotica speciosa*). Other examples of Coleoptera include *Agroites mancus, Limonius agonu*, white grub, *Chaetocnema pulicaria, Carpophilus lugubris, Popilia japonica, Epitrix cucumeris, Epitrix fuscula, Systena blanda, Cerotoma trifurcate, Epilachna varivestis, Phyllotreta striolata, Phyllotreta cruciferae, Acalymma vittata, Metriona bicolor, Systena blanda, Crioceris asparagi, Crioceris duodecimpunctata, Disonycha xanthomelas, Epitrix* spp., and *Epicauta* spp.

Examples of Diptera include *Delia platura, Zonosemata electa, Delia radicum, Delia antique, Liriomyza sativae, Pegomya hyoscyami, Anopheles* spp., *Aedes* spp., *Culex* spp., *Onchocerca volvulus, Phlebotomus* spp., Lutzomyia spp., *Chrysops* spp., *Tabanus* spp., *Glossina* spp., *Musca domestica*, and *Stomoxys* spp.

Further, there are numerous parasitic nematode species, including various cyst nematodes (e.g. *Heterodera* spp. or *Globodera* spp.), root knot nematodes (e.g. *Meloidogyne* spp.), lesion nematodes (e.g. *Pratylenchus* spp.), dagger nematodes (e.g. *Xiphinema* spp.) and stem and bulb nematodes (e.g. *Ditylenchus* spp.), among others. *Tylenchid* nematodes (members of the order Tylenchida), including the families Heteroderidae, Meloidogynidae, and Pratylenchidae, are the largest and most economically important group of plant-parasitic nematodes. Other important parasitic nematodes include reniform nematodes (*Rotylenchulus* species) and *Dorylaimid* nematodes (e.g. *Xiphinema* spp.), among others. Thus improved control of nematodes via multifunctional toxins is also contemplated.

Pathogenic microorganisms contemplated for control may belong to any family of organisms such as, but not limited to prokaryotic organisms, *Eubacterium*, archaebacterium, eukaryotic organisms, yeast, fungi, algae, protozoan, and other parasites. Non-limiting examples of pathogenic microorganism are *Plasmodium falciparum* and related malaria-causing protozoan parasites, *Acanthamoeba* and other free-living amoebae, *Aeromonas hydrophile, Anisakis* and related worms, *Acinetobacter baumanii, Ascaris lumbricoides, Bacillus cereus, Brevundimonas diminuta, Campylobacter jejuni, Clostridium botulinum, Clostridium perfringens, Cryptosporidium parvum, Cyclospora cayetanensis, Diphyllobothrium, Entamoeba histolytica*, certain strains of *Escherichia coli, Eustrongylides, Giardia lamblia, Klebsiella pneumoniae, Listeria monocytogenes, Nanophyetus, Plesiomonas shigelloides, Proteus mirabilis, Pseudomonas aeruginosa, Salmonella, Serratia odorifera, Shigella, Staphylococcus aureus, Stenotrophomonas maltophilia, Streptococcus, Trichuris trichiura, Vibrio cholerae, Vibrio parahaemolyticus, Vibrio vulnificus* and other vibrios, *Yersinia enterocolitica, Yersinia pseudotuberculosis* and *Yersinia kristensenii.*

Illustrative prokaryotes, both Gram-negative and Gram-positive, may include Enterobacteriaceae, such as *Erwinia*; Bacillaceae; Rhizobiaceae, such as *Rhizobium*; Spirillaceae, such as photobacterium, *Zymomonas*; Lactobacillaceae; Pseudomonadaceae, such as *Acetobacter*; Azotobacteraceae, Actinomycetales, and Nitrobacteraceae. Also among eukaryotes are fungi, such as *Phycomycetes* and *Ascomycetes*, including *Saccharomyces* and *Schizosaccharomyces*; and *Basidiomycetes*, such as *Rhodotorula, Aureobasidium*, and the like.

In some aspects, this disclosure provides pest control methods comprising providing to a pest a variant Bt toxin. Methods of pest control described herein may therefore be useful for controlling pests that are resistant to treatment with certain known and available wild-type Bt toxins.

Historically, Bt toxin has been used to control populations of pests that damage crops. For example Bt toxin can be topically applied to plants affected by pests as an insecticide. In other cases, plants, such as corn (*Zea mays*), cotton (*Gossypium* sp.), rice (*Oryza sativa* L.), alfalfa (*Medicago sativa*), potato (*Solanum tuberosum*), tomato (*Solanum lycopersicum*), soybean (*Glycine max*), tobacco (*Nicotiana* sp.), canola (*Brassica napus*) and other *Brassica* sp., or other crop plants can be genetically modified to express one or more Bt toxin(s). Thus, in some embodiments, the disclosure provides cells and/or plants and/or seeds comprising a variant Bt toxin or the nucleic acid sequence encoding such a variant, e.g., in the form of a variant Bt toxin expressed from a recombinant nucleic acid encoding a variant Bt toxin provided herein. In some embodiments, the cell is a plant cell. Suitable methods of engineering plant cells and plants to express genes, including wild-type Bt genes, are well known to those of skill in the art, and such methods can be used to produce plant cells and plants expressing the Bt toxin variants provided herein. Additionally, a commodity product produced from such a plant, and comprising a detectable amount of a multifunctional protein as described herein, is also contemplated as an aspect of the invention. Such commodity products may include, without limitation, seeds, fruit, stems, leaves, tubers, or roots of such a plant, optionally further processed to result in, for instance, flour, meal, or oil for consumption by an animal, or for industrial use, for instance as a fuel or lubricant.

Methods for producing a transgenic plant which expresses a nucleic acid segment encoding a novel Bt toxin variant as described herein can be achieved utilizing variations of methods well known in the art. In general, such a method comprises transforming a suitable host cell with a DNA segment which contains a promoter operably linked to a coding region that encodes one or more of the Bt toxin variants. Such a coding region is generally operably linked to a transcription-terminating region, whereby the promoter is capable of driving the transcription of the coding region in the cell, and hence providing the cell the ability to produce the polypeptide in vivo. Vectors, plasmids, cosmids, and DNA segments for use in transforming such cells will generally comprise operons, genes, or gene-derived sequences, either native, or synthetically-derived, and particularly those encoding the disclosed Bt toxin variant proteins. These DNA constructs can further include structures such as promoters, enhancers, polylinkers, or other gene sequences which can have regulating activity upon the particular genes of interest. Without limitation, examples of plant transformation vectors include those derived from a Ti plasmid of *Agrobacterium tumefaciens*, as well as those disclosed, e.g., by Herrera-Estrella (*Nature* 303:209-213, 1983), Bevan (Nature 304:184-187, 1983), Klee (*Bio/Technol.* 3:637-642, 1985). Such transgenic plants are desirable for increasing the insecticidal resistance of a monocotyledonous or dicotyledonous plant, by incorporating into such a plant, a transgenic DNA segment encoding one or more Bt toxin variant proteins which are toxic to insects. In a related aspect, the present method also encompasses a seed produced by the transformed plant, a progeny from such seed, and a seed produced by the progeny of the original transgenic plant, produced in accordance with the above process. Such progeny and seeds will have a Bt toxin variant protein-encoding transgene stably incorporated into their genome, and such progeny plants expressing the encoded protein would inherit and display the insect control trait or traits afforded by the introduction of such a transgene.

Further aspects of the invention relate to recombinant DNA constructs for expression of a multi-functional pest control protein as herein described. Such a protein may be expressed in a host cell such as a bacterial cell or a plant cell. Recombinant host cells, including bacterial cells and plant cells, comprising such a recombinant construct, are thus also contemplated, as is the multi functional protein produced by the host cell. A resulting protein may be produced for ingestion in the diet of a target pest organism, or by otherwise contacting a target pest, such as a target insect pest, with a multi functional protein as described herein. Topical application of a composition comprising such a multi functional protein is also contemplated. Such application may be performed directly onto a target organism, or the composition may be applied to the environment of a target organism and may thus subsequently contact the organism. Thus such compositions, and methods for producing and formulating such compositions for topical application, are also contemplated. Such a composition may also, for instance, comprise another Bt toxin, as well as one or more other pest control molecule displaying one or more other mode(s) of action (e.g. a chemical active against a target organism of interest).

Examples of techniques for introducing DNA into plant tissue are disclosed in European Patent Application Publication No. 0 289 479, published Nov. 1, 1988, and by Perlak et al. in "Modification of the Coding Sequence Enhances Plant Expression of Insect Control Protein Genes," Proc. Natl. Acad. Sci. USA, 88, pp. 3324-3328 (1991). Examples of methods which can be modified for obtaining transgenic plants that express insect-active proteins include those describing, for example, Cry1A proteins (U.S. Pat. No. 5,880,275), Cry1B (U.S. Patent Application Publication No. 2006/0112447), Cry1C (U.S. Pat. No. 6,033,874), Cry1A/F chimeras (U.S. Pat. Nos. 7,070,982; 6,962,705, and 6,713,063), and a Cry2Ab protein (U.S. Pat. No. 7,064,249).

Phage assisted continuous evolution (PACE) is a particular method for directed evolution that creates and selects for protein variants with a desired activity (Esvelt, et al. *Nature* 472, 499-503, 2011). PACE selects for protein-protein interactions by utilizing engineered *E. coli* and M13 bacteriophage that express a component of a bacterial 2-hybrid system that links the strength of interaction to the fitness of the phage. *E. coli* cells carries two plasmids: the accessory plasmid (AP), which links protein binding to phage propagation and controls selection stringency, and the mutagenesis plasmid (MP), which enables inducible mutagenesis to provide variation. The selection phage (SP) encode an evolving protein that interacts with the target protein and results in the production of pIII, a phage protein required for infectivity of progeny phage. PACE takes place in a fixed-volume vessel that is continuously diluted with fresh host cells. SP encoding protein variants that bind the target propagate faster and become more abundant while SP encoding variants that do not interact with the target propagate at a slower rate and become progressively less abundant. This dynamic prevents the co-evolution of the target and provides continuous selection on the evolving protein.

Certain embodiments of the invention take advantage of recent discoveries enabling modification and insertion of segments directly into the genome of the plant without introduction of a transgene using traditional *Agrobacterium* or ballistic mediated methods, and these are referred to in the art as gene editing and site directed integration. It is within the skill of the art to modify the transgenic DNA present within a transgenic plant, i.e. make modifications for example to a locus within the plant genome that has been introduced and is enabled for the encoding a toxin, and introduce changes into that transgene within the plant. For example, with reference to the embodiments within this application, it is now possible to modify the gene in a cotton plant that expresses a Cry1Ac1 protein, to which any particular lepidopteran target species pest of cotton has developed field resistance, and introduce modifications to the in-planta gene (i.e., edit the gene) that will result in a new nucleotide sequence in the transgene locus that encodes a modified Cry1Ac1 protein that is now capable of binding to a receptor not previously bound by the native Cry1Ac1 in the resistant target species pest of cotton and restore the sensitivity to Cry1Ac1 to the Cry1Ac1 insensitive target species pest. Thus restoring to the transgenic plant the ability to control the pest that has become resistant to the original toxin and to provide two or more modes of action for controlling the pest as a result of the ability of the modified toxin to bind to two or more different receptors. This increases the durability of the plant as well and increases the efficacy of the transgenic plant.

Production of a protein of the present invention in a transgenic plant or plant cell can be combined with means for expressing at least one other gene(s) encoding other protein toxins or pesticidal agents that have been shown to target for control the same or even a different pest. For example, a plant expressing a Bt toxin for controlling a corn earworm may be engineered to contain a modified Bt toxin that binds to two or more different receptors in a corn earworm gut, thus providing for two or more modes of action for controlling a corn earworm pest with a single protein. This engineered plant, if a corn plant, can then be combined with any number of transgenic events known in the art such as MON810, MON89034, MIR162, TC-1507, and the like to provide for an additional Bt toxin effective for controlling corn earworm and other lepidopteran pests of corn. Furthermore, the toxin coding sequences in these events can be engineered to exhibit two or more modes of action for each of the encoded toxin proteins, such as Cry1Ab, Cry1A.105, Cry2Ab, VIP3Aa and Cry1F, providing for durability and greater efficacy of each of these events in the market place. Such corn plants controlling lepidopteran species can be combined with one or more transgenes that control other pests such as a Coleopteran pest, for instance corn rootworms, exemplified by current commercial transgenic events such as MON88017, DAS-59122-7, and MIR164, which each in turn can be engineered using the methods taught herein to modify the encoded rootworm toxins in each of these embodiments to exhibit two or more modes of action, each such protein binding at least one additional target receptor in a corn rootworm gut to give effect to a more durable product, and to enhance the efficacy of the products as a result of the toxin proteins encoded by these transgenic events to bind to more than one receptor in the target insect gut.

Cells comprising variant Bt toxin can be isolated (i.e., cultured or stored in vitro), or can form part of a plant (e.g., a transgenic plant expressing a variant Bt toxin) or an entire plant, rendering the respective plant resistant to pests susceptible to the variant Bt toxin. Such pests may include, in some embodiments, pests that are resistant or refractory to wild-type Bt toxin.

As used herein, the term "isolated DNA molecule" means that the DNA molecule is present alone or in combination with other compositions but is not within its natural environment. For example, a DNA recombinant molecule comprising a protein-coding sequence and heterologous chloroplast transit peptide sequence is considered isolated when it is found in a context that is not the genome in which it is naturally found. Such a recombinant DNA molecule would be an isolated DNA molecule when present in the genome of a transgenic plant, the components of that recombinant DNA molecule being thus not in their natural environment (that is, the genome of the organism from which the structure was first observed). A recombinant DNA molecule of the invention thus would be an isolated DNA molecule so long as the recombinant DNA molecule was not within the DNA of the organism from which the structure was first observed.

In certain embodiments the present invention also provides a pesticidal protein that comprises a multifunctional variant of Cry1Ac1 (SEQ ID NO:1) selected from the group consisting of Protein 3 (SEQ ID NO:2), Protein 4 (SEQ ID NO:3), Protein 5 (SEQ ID NO:4). The present invention also provides a pesticidal protein that comprises a multifunctional variant of TIC2160 (SEQ ID NO:5), comprising TIC2160* (SEQ ID NO:7).

The present invention also provides a cadherin binding peptide selected from the group consisting of SEQ ID NO:6 and SEQ ID NO:9. These cadherin binding peptides, when inserted into a pesticidal protein, allow for the additional functionality of being able to bind to cadherin receptors in insect cells.

The present invention also provides a pesticidal protein that comprises a multifunctional variant of Cry1Ac1 (SEQ ID NO:1), comprising SEQ ID NO:11. The present invention also provides a pesticidal protein that comprises a multifunctional variant of TIC105 (SEQ ID NO:8), selected from the group consisting of SEQ ID NO:10 and SEQ ID NO:12. The present invention also further provides a chimeric cadherin receptor comprising SEQ ID NO: 13.

EXAMPLES

The function and advantage of these and other embodiments of the present invention will be more fully understood from the examples described below. The following examples are intended to illustrate the benefits of the present invention and to describe particular embodiments, but are not intended to exemplify the full scope of the invention. Accordingly, it will be understood that the examples are not meant to limit the scope of the invention.

Example 1

PACE Evolved Cry1Ac1 with Additional MOA

A variant CryAc1 protein with an additional mode of action (MOA) was produced by PACE directed evolution (Esvelt, et al. *Nature* 472, 499-503, 2011). The *Bacillus thuringiensis* endotoxin Cry1Ac (SEQ ID NO:1) does not natively bind to the cadherin receptor from the insect pest *Trichoplusia ni* (TnCAD). Badran et al. (*Nature* 533, 58-63, 2016) demonstrated that PACE derived variants of Cry1Ac gained affinity for TnCAD. These variants are more toxic to wild-type-Cry1Ac-resistant *T. ni* than wild-type Cry1Ac.

Cultured *Spodoptera frugiperda* (Fall Armyworm, "FAW") Sf9 cells (Vaughn et al., *In Vitro* 13:213-217, 1977), transformed to express selected proteins that act as toxin receptors upon expression in the Sf9 cells and display on the surface of the Sf9 cells, were used to test for binding of various Cry1Ac protein toxin amino acid sequence variants. This binding was compared to binding of the native Cry1Ac toxin protein. Successful binding of a toxin, such as a variant protein, to the surface receptor on the Sf9 cell causes pore formation. The resulting pore allows an added fluorophore to enter the cell via the compromised cell membrane and bind to DNA, causing the cells with pores to fluoresce under appropriate lighting conditions.

Such fluorescence can be compared to background fluorescence levels of appropriate controls, and thus utilized to detect toxin activity. Fluorescence intensity in Sf9 cells expressing any particular receptor to which a variant pesticidal protein may bind is expected to correlate with pesticidal activity.

All amino acid residue substitutions described in this application are with reference to those positions as set forth above in the Cry1Ac core toxin amino acid sequence. For instance, for Cry1Ac the core sequence is from residues 29 to 620 in SEQ ID NO:1.

Native (wild-type) Cry1Ac functionally interacts (i.e. binds) with the FAW ABCc2 and ABCc3 transporters, leading to an increased SYTOX® Green (ThermoFisher Scientific, Waltham, MA, USA) fluorescent signal detectable in Sf9 cell cultures expressing those transporters. Native Cry1Ac does not functionally interact with cabbage looper cadherin or soybean looper cadherin. Selected Cry1Ac amino acid sequence variants retain their functional interaction with FAW ABCc2 and ABCc3, while acquiring a new functional interaction with soybean looper cadherin and cabbage looper cadherin.

Cry1Ac1 variants were tested for relative toxicity in insect cell-based assays. Lawns of Sf9 cells, engineered to express cadherin from *T. ni* (cabbage looper, Table 3) or soybean looper (*Chrysodeixis includens* also known as *Pseudoplusia includens*, Table 4), were overlayed with a composition containing cell membrane-impermeable SYTOX® Green dye that fluoresces when it binds with DNA. Cry1Ac amino acid sequence variant proteins were pre-treated with trypsin to release the three-domain Cry1Ac toxic core. The toxicity of Cry1Ac1 and its variants to Sf9 cells expressing *T. ni* (cabbage looper) cadherin, was measured by increased fluorescence intensity of SYTOX® Green dye. Protein concentrations are shown for each toxin. Designated names for certain PACE-evolved variants C02, C03, C05, C09, A01 and A02 (e.g. Badran et al., 2016) are given in Table 1. Each data point is the mean of three measurements, with calculated standard deviation (SD) shown.

Table 1 illustrates the fluorescence intensity caused by presence of Cry1Ac1 and Cry1Ac amino acid sequence variants in Sf9 cells expressing *T. ni* (cabbage looper) cadherin (Table 1A) or *C. includens* (soybean looper) cadherin (Table 1B), as measured by increased relative fluorescence intensity of SYTOX® Green dye. Protein concentrations are shown for each toxin. Cry1Ac amino acid sequence variants (C02, C03, C05, C09, A01 and A02) were tested. As shown in Tables 1A and 1B, the fluorescence intensity of SYTOX® Green dye utilized to measure toxin-induced cellular pore formation in Sf9 cells expressing these various cadherins and exposed to different variants resulted in increased fluorescence of 2 to 40 times the level of fluorescence compared to control cells using wild type Cry1Ac1 (wt-Cry1Ac1). Thus, certain residues in Cry1Ac can be targeted for modification to obtain a protein toxin that exhibits binding to lepidopteran insect cadherin, which binding results in the protein toxin forming a pore in the membrane that allows the fluorophore to enter the Sf9 cells, bind to cellular DNA, and fluoresce.

TABLE 1A

Fluorescence Intensity of Sf9 cells expressing *T. ni* cadherin Exposed to Cry1Ac amino acid sequence variants.

| | Amino acid substitutions relative to Cry1Ac | Relative fluorescence | Standard deviation |
| --- | --- | --- | --- |
| Buffer | | 473 | 22 |
| Empty vector | | 766 | 113 |
| Cry1Ac1, 28 ug/ml | | 549 | 90 |
| Cry1Ac1_D384Y_S404C, 16 ug/ml | D384Y_S404C | 1041 | 61 |
| Cry1Ac1_C02, 7 ug/ml | D384Y_S404C_E461K_N463S_E332G_T304N_A344E_T361I_S582L_F68S_G286D_C15W | 6939 | 120 |
| Cry1Ac1_C03, 4 ug/ml | D384Y_S404C_E461K_N463S_T304N_A344E_T361I_S582L_C15W_M322K_Q353H_F68S_G286D_E332G | 7590 | 455 |
| Cry1Ac1_C05, 9 ug/ml | D384Y_S404C_C15W_T304N_A344E_T361I_E461K_N463S_S582L | 8189 | 708 |
| Cry1Ac1_C09, 3 ug/ml | D384Y_S404C_R198G_S363P_N417D_E332G_E461K_N463S_S582L_T386A | 4929 | 281 |
| Cry1Ac1_A01, 4 ug/ml | D384Y_S404C_E461K_N463S_T304N_A344E_T361I_S582L_C15W_M322K_Q353H | 10591 | 613 |
| Cry1Ac1_A02, 1 ug/ml | D384Y_S404C_R198G_S363P_N417D_E332G_E461K_N463S_S582L | 5425 | 385 |

TABLE 1B

Fluorescence Intensity of Sf9 cells expressing *C. includens* cadherin exposed to Cry1Ac amino acid sequence variants.

| | Amino acid substitutions relative to Cry1Ac | Relative fluorescence | Standard deviation |
|---|---|---|---|
| Buffer | | 546 | 191 |
| Empty vector | | 407 | 70 |
| Cry1Ac1, 28 ug/ml | | 116 | 47 |
| Cry1Ac1_D384Y_S404C, 16 ug/ml | D384Y_S404C | 180 | 115 |
| Cry1Ac1_C02, 7 ug/ml | D384Y_S404C_E461K_N463S_E332G_T304N_A344E_T361I_S582L_F68S_G286D_C15W | 4468 | 697 |
| Cry1Ac1_C03, 4 ug/ml | D384Y_S404C_E461K_N463S_T304N A344E_T361I_S582L_C15W_M322K_Q353H_F68S_G286D_E332G | 3425 | 624 |
| Cry1Ac1_C05, 9 ug/ml | D384Y_S404C_C15W_T304N_A344E_T361I_E461K_N463S_S582L | 3391 | 69 |
| Cry1Ac1_C09, 3 ug/ml | D384Y_S404C_R198G_S363P_N417D_E332G_E461K_N463S_S582L_T386A | 3286 | 649 |
| Cry1Ac1_A01, 4 ug/ml | D384Y_S404C_E461K_N463S_T304N_A344E_T361I_S582L_C15W_M322K_Q353H | 4287 | 572 |
| Cry1Ac1_A02, 1 ug/ml | D384Y_S404C_R198G_S363P_N417D_E332G_E461K_N463S_S582L | 3642 | 284 |

Example 2

The Cry1Ac1 Toxin Variants are Multifunctional, and Retain the Ability to Also Functionally Bind to FAW ABC Transporters Cry1Ac is known to bind to the transporter proteins ABCc2 and ABCc3, which can thus be considered to be receptors for the wild type Cry1Ac protein. Data shown in Table 2A and Table 2B demonstrate how the modifications introduced into the Cry1Ac protein as shown in Tables 1 and 2 affect interaction of variant Cry1Ac with receptors ABCc2 and ABCc3.

The results below show that variants that were tested and compared to wild-type Cry1Ac1 using the Sf9/green dye assay as in Example 1, but with Sf9 cells expressing either FAW ABCc2 or ABCc3 transporter proteins (the insect receptor for wild-type-Cry1Ac1), retained ability to bind to these receptors and induce fluorescent dye uptake. This demonstrates that the various amino acid changes introduced into Cry1Ac1 as shown in Example 1, which provided for Cry1Ac1 binding to the *C. includens* or *T. ni* cadherins, did not result in the loss of function of binding to the FAW receptors. Protein 3 (SEQ ID NO:2) is the _C05 variant protein from Example 1; Protein 4 (SEQ ID NO:3) is the _C03 protein from Example 1, and Protein 5 (SEQ ID NO:4) is the _A01 protein from Example 1; except that, in this example, these polypeptides did not contain the D384Y or the S404C modification which was separately found to cause proteolytic instability in the resulting Cry1Ac1 variant, but which did not result in significant difference in functional activity when used only in bioassay with the Sf9 cell assay.

TABLE 2A

Fluorescence Intensity of Sf9 cells expressing *Spodoptera frugiperda* ABCc2 transporter Exposed to Cry1Ac amino acid sequence variants.

| Toxin | Toxin concentration, ug/ml | Relative fluorescence, mean | Standard deviation |
|---|---|---|---|
| Buffer control | 0 | 4182 | 820 |
| Cry1Ac1 | 0.05 | 58938 | 921 |
| Cry1Ac1 | 0.2 | 82515 | 2377 |
| Cry1Ac1 | 0.5 | 100136 | 1868 |
| Protein 3 | 0.05 | 68972 | 856 |
| Protein 3 | 0.2 | 87408 | 1100 |
| Protein 3 | 0.5 | 118592 | 6151 |
| Protein 4 | 0.05 | 75437 | 2228 |
| Protein 4 | 0.2 | 94713 | 1501 |
| Protein 4 | 0.05 | 75437 | 2228 |
| Protein 5 | 0.05 | 69133 | 1435 |
| Protein 5 | 0.2 | 86085 | 2642 |
| Protein 5 | 0.5 | 112897 | 2979 |

TABLE 2B

Fluorescence Intensity of Sf9 cells expressing *Spodoptera frugiperda* ABCc3 transporter Exposed to Cry1Ac amino acid sequence variants.

| Toxin | Toxin concentration, ug/ml | Relative fluorescence, mean | Standard deviation |
|---|---|---|---|
| Buffer control | 0 | 11 | 164 |
| Cry1Ac1 | 0.2 | 45252 | 139 |
| Cry1Ac1 | 1 | 92852 | 3978 |
| Cry1Ac1 | 5 | 121659 | 1659 |
| Protein 3 | 0.2 | 24070 | 782 |
| Protein 3 | 1 | 67187 | 1598 |
| Protein 3 | 5 | 115760 | 2671 |
| Protein 4 | 0.2 | 7965 | 66 |
| Protein 4 | 1 | 26474 | 1404 |
| Protein 4 | 5 | 79866 | 1172 |
| Protein 5 | 0.2 | 39769 | 563 |
| Protein 5 | 1 | 84305 | 1372 |
| Protein 5 | 5 | 119408 | 2195 |

Cry1Ac toxin binding to the *S. frugiperda* ABCc2 and ABCc3 transporters is thus retained in the variant toxin proteins and the variants of Cry1Ac retain pore forming ability which allows the fluorophore to accumulate in the Sf9 cells.

Example 3

Cry1Ac1 Variants Exhibiting Two or More Modes of Action (MOA's) on Cabbage Looper Larvae The toxic dose required to kill Cry1Ac1-sensitive loopers and Cry1Ac1-resistant loopers was compared to demonstrate that Cry1Ac1 variants exhibit multiple modes of action (MOA's) on cabbage looper larvae. Provided data also distinguishes between two possible explanations for the observations: that a given Cry1Ac amino acid sequence variant that binds to cadherin may have enhanced affinity to a single receptor, and thus only provides a single mode of action; alternatively, the variant may be binding to two different receptors and therefore would confer two different modes of action for pore forming activity. To distinguish these possibilities, diet bioassays were conducted with *T. ni* larvae of two lines. One line exhibits resistance to Cry1Ac, and the other (wild-type) line is sensitive to Cry1Ac. Larvae were exposed to sucrose gradient purified toxin crystals in a standard diet bioassay (e.g. Baum et al., *J. Econ. Entomol.* 105:616-624, 2012). The results are shown in Table 3.

In Table 3, proteins 1 and 2 correspond to the _C03 and _C05 proteins respectively as shown in Example 1, however as discussed in Example 2, these particular polypeptides contain additional amino acid substitutions (D384Y or the S404C) that may lead to increased proteolysis, and so displayed reduced relative activity in these bioassays. In contrast the corresponding variants that lack these proteolytic instability inducing amino acid substitutions, Protein 4 and Protein 3 respectively (_C03 and _C05 as in Example 1 but lacking D384Y and S404C) as well as Protein 5 (_A01) yield high relative potency scores as shown in Table 3, indicating efficacious binding of the variant Cry1Ac1 to the respective *T. ni* larvae.

Results of diet bioassay with *T. ni* (Table 3) illustrate the activity (mortality and growth inhibition) of Cry1Ac1 variants (utilized as sucrose gradient purified Bt crystals) in diet bioassay compared to native Cry1Ac. The LC50 data for the Cry1Ac susceptible cabbage looper larvae indicate that the proteins have been engineered to exhibit a second mode of action. A decrease in apparent activity seen for proteins 3-5 on resistant *T. ni*, as compared to susceptible *T. ni*, may be explained as due to binding to only a single receptor in the resistant insect cells, whereas for Cry1Ac1-susceptible *T. ni* the toxin is binding at least two different receptors, resulting in differences in effective dose on the different *T. ni* lines.

The LC50 range for the engineered Cry1Ac amino acid sequence variants is 0.018-0.025 on the Cry1Ac susceptible *T. ni* colony and 0.153-1.938 on the Cry1Ac resistant colony. This data is consistent with the presence of multiple modes of action in the engineered proteins, i.e. there are n MOA's available in the susceptible colony in the presence of the Cry1Ac amino acid sequence variants (the colony that is sensitive to the wild type Cry1Ac), and there are n−1 MOA's available in the resistant colony in the presence of the Cry1Ac amino acid sequence variants (the colony that has evolved resistance to the wild type Cry1Ac). The data also suggests that a pesticidal protein that acts to confer its effects upon a target pest by binding to two or more different receptors in that pest may provide for the delivery of a decreased minimum effective dose when both receptors are present. Such proteins can confer upon a plant producing a pesticidally effective amount of the pesticidal protein the ability to deliver a more efficacious dose to any particular susceptible target pest, and to provide a more durable form of insect control because the protein is providing its effects through multiple modes of action and it will be less likely that any single pest would become resistant to the more than one mode of action conferred by the protein.

TABLE 3

Insecticidal activity of Cry1Ac amino acid sequence variants against Cry1Ac-resistant and susceptible *Trichoplusia ni*.

| | | Toxin | LC50 | 95% CL | Slope | SE | Relative potency (%) |
|---|---|---|---|---|---|---|---|
| Susceptible *T. ni* | Response: Mortality | Cry1Ac | 0.039 | 0.019-0.069 | 2.54 | 0.26 | 100 |
| | | Protein 1 | 0.793 | 0.505-1.082 | 2.84 | 0.41 | 5 |
| | | Protein 2 | 0.715 | 0.407-1.176 | 1.78 | 0.22 | 5 |
| | | Protein 3 | 0.035 | 0.026-0.045 | 3.59 | 0.41 | 111 |
| | | Protein 4 | 0.018 | 0.014-0.020 | 4.68 | 0.75 | 217 |
| | | Protein 5 | 0.021 | 0.015-0.024 | 4.82 | 1.09 | 186 |
| | Response: growth inhibition | Cry1Ac | 0.019 | 0.011-0.027 | 3.09 | 0.39 | 100 |
| | | Protein 1 | 0.136 | 0.110-0.160 | 4.00 | 0.62 | 14 |
| | | Protein 2 | 0.217 | 0.167-0.268 | 2.59 | 0.32 | 9 |
| | | Protein 3 | 0.016 | 0.014-0.018 | 5.53 | 0.82 | 119 |
| | | Protein 4 | 0.007 | 0.003-0.010 | 3.65 | 0.61 | 271 |
| | | Protein 5 | 0.005 | 0.004-0.006 | 4.92 | 0.90 | 380 |
| Cry1Ac resistant *T. ni* | Response: Mortality | Cry1Ac | 51.229 | 9.929-90.241 | 1.89 | 0.36 | 100 |
| | | Protein 1 | 408.713 | 263.629- | 0.81 | 0.10 | 13 |
| | | Protein 2 | 235.698 | 79.467-510.323 | 1.12 | 0.15 | 22 |
| | | Protein 3 | 1.938 | 1.550-2.352 | 2.55 | 0.29 | 2643 |
| | | Protein 4 | 1.841 | 1.390-2.312 | 2.25 | 0.28 | 2783 |
| | | Protein 5 | 0.153 | 0.046-0.289 | 2.01 | 0.22 | 33483 |
| | Response: growth inhibition | Cry1Ac | 23.402 | 4.587-46.512 | 1.49 | 0.25 | 100 |
| | | Protein 1 | 56.626 | 40.600-75.685 | 1.84 | 0.21 | 41 |
| | | Protein 2 | 47.232 | 20.236-90.729 | 1.16 | 0.12 | 50 |
| | | Protein 3 | 1.116 | 0.797-1.484 | 2.19 | 0.23 | 2097 |
| | | Protein 4 | 0.733 | 0.515-0.949 | 2.06 | 0.28 | 3193 |
| | | Protein 5 | 0.083 | 0.061-0.104 | 2.57 | 0.38 | 28195 |

Example 4

Modifying TIC2160 to Provide an Additional Mode of Action

Lepidopteran active toxin TIC2160 (SEQ ID NO:5), lacks substantial insecticidal or insect growth-inhibiting activity when tested in bioassay against fall armyworm larvae. However, it is demonstrated herein that, by introducing a peptide sequence, selected for its ability to bind with high affinity to the Sf cadherin, into domain IV of the TIC2160 protein, an increased activity of the modified TIC2160 protein is seen. The modified TIC2160 protein thus displays an additional mode of action.

TIC2160 is an insect control protein that is toxic to a number of Lepidopteran species, and is derived from a Bacillus species (PCT/US2015/055802). However, this protein displays little activity when tested against fall armyworms in laboratory bioassays.

A Sf cadherin protein (Sf CAD) was isolated and a specific 12 amino acid segment that demonstrated tight binding to Sf CAD was identified. Introgression of the 12-mer segment into the TIC2160 protein structure at several predicted loop regions within the TIC2160 protein was performed, and the resulting candidate molecules were tested for their ability to maintain lepidopteran specific toxic properties. A location in Domain IV of the TIC2160 protein was identified that supported the introgression of the 12-mer amino acid sequence NH3-Val-Asp-Trp-Trp-Ser-Pro-Phe-Tyr-Asp-Arg-Leu-Lys-COOH (SEQ ID NO:6). The resulting protein TIC2160* (SEQ ID NO:7) was tested at 250 ppm in diet bioassays against Sf larvae. The diet bioassay was evaluated to measure the effect of a toxin on insect growth, or decreased growth (stunting). 20 to 30 insects were evaluated in each dosing group (or control group); insect size was evaluated after one week on the diet with or without toxin added. Size was evaluated as the number of pixels generated per insect using a high resolution digital camera image. Larvae that received empty vector control or untreated control were not stunted. A positive control lepidopteran active protein known for bioactivity against Sf and also tested at 250 ppm showed about 55% stunting relative to controls. The unmodified wild type TIC2160 exhibited about 25% stunting, and the TIC2160* proteins all exhibited about 80-85% stunting. Thus inclusion of the twelve amino acid peptide into Domain IV of the TIC2160 protein provided a new mode of action for this protein with respect to Sf larvae.

Example 5

Modifying Additional Lepidopteran Active Toxins to Provide an Additional Mode of Action Modification of lepidopteran active toxins TIC105 (SEQ ID NO:8; see U.S. Pat. No. 8,034,997, referred to therein as Cry1A.105) and Cry1Ac1 (SEQ ID NO:1) was also performed.

S. frugiperda Sf9 cells in culture were transformed with proteins that act as toxin receptors, to test for binding of various Cry1Ac and TIC105 protein toxin amino acid sequence variants. Binding of such modified proteins was compared to that of the native Cry1Ac (SEQ ID NO:1) and TIC105 (SEQ ID NO:8) toxin protein. As noted above the binding of a modified toxin to the surface receptor on the Sf9 cell causes pore formation; the resulting pore allows a fluorophore to enter the insect cell and the cells can display increased fluoresce under the appropriate lighting conditions. Resulting fluorescence can be compared to background fluorescence of control cells. All amino acid residue insertions-replacements referenced in this application are with reference to those positions as set forth above in the Cry1Ac and TIC105 toxin amino acid sequence.

Cry1Ac and TIC105 display a functional interaction with the S. frugiperda ABCc2 transporter leading to an increased SYTOX® Green dye fluorescence signal in Sf9 cells expressing those transporters. Cry1Ac and TIC105 do not display a natural functional interaction with S. frugiperda cadherin. Cry1Ac and TIC105 amino acid sequence variants, created by inserting a peptide sequence that binds to S. frugiperda cadherin into Cry1Ac and TIC105 scaffolds, retain their functional interaction with FAW ABCc2. Further, some variants acquire new functional interaction with S. frugiperda cadherin. Fluorescence intensity in Sf9 cells expressing any particular receptor to which a pesticidal protein will bind is expected to correlate with pesticidal activity.

Cry1Ac1 and TIC105 S. frugiperda binding variants were tested for relative toxicity in insect cell-based assays. Lawns of Sf9 cells, engineered to express cadherin from S. frugiperda were overlayed with a composition containing membrane-impermeable SYTOX® Green dye and Cry1Ac- or TIC105-amino acid sequence variants, pretreated with trypsin to release the three-domain toxic core (for Cry1Ac the core is from residues 29 to 620 in SEQ ID NO:1; for TIC105 the core is from residues 29 to 619 in SEQ ID NO:8). Variants which bind to cadherin receptors aggregate to form pores, allowing the dye to enter the compromised cell membrane. The dye can then bind to DNA and result in intense green fluorescence. The toxicity of Cry1Ac1, TIC105 and its variants to Sf9 cells expressing S. frugiperda cadherin was inferred by increased fluorescence intensity of SYTOX® Green dye.

The TIC105 variant of SEQ ID NO:10 comprises the Sf cadherin binding protein of SEQ ID NO:9 inserted into the TIC105 scaffold (SEQ ID NO:8), in place of the three residues from G342 to A344. Testing this variant in cells expressing S. frugiperda cadherin demonstrated that addition of S. frugiperda cadherin binding peptide (SEQ ID NO:9) resulted in increased fluorescence intensity of approximately 4 times the level of fluorescence seen with control cells using wild type unmodified TIC105 (SEQ ID NO:8). At the same time the TIC105 variant (SEQ ID NO:10) was as active as wild-type unmodified TIC105 (SEQ ID NO:8) against cells expressing FAW ABCc2 receptor.

The Cry1Ac1 variant in SEQ ID NO:11, comprises the Sf cadherin binding protein of SEQ ID NO:6 inserted into the Cry1Ac1 scaffold (SEQ ID NO:1), following residue N343. Testing this variant in cells expressing S. frugiperda cadherin showed that addition of S. frugiperda cadherin binding peptide (SEQ ID NO:6) resulted in increased fluorescence intensity of 4 to 5 times the level of fluorescence compared to control cells using wild type unmodified Cry1Ac1 (SEQ ID NO:1). At the same time the Cry1Ac1 variant (SEQ ID NO:10) was as active as wild type unmodified TIC105 (SEQ ID NO:8) against cells expressing FAW ABCc2 receptor. Thus the TIC105 and Cry1Ac1 toxin variants, comprising SEQ ID NOs:10 or 11, are multifunctional toxins engineered to be effective against cells expressing Sf cadherin while retaining activity against cells expressing the Sf ABCc2 transporter.

Example 6

PACE Evolved TIC105 with Additional MOA

TIC105 (SEQ ID NO:8), a chimera toxin of Cry1Ab-1Ab-1Fa binds to the transporter proteins FAW ABCc2 and APN1/ABCc3, considered to be receptors for the wild-type TIC105 protein. TIC105 does not bind the cadherin receptor of *S. frugiperda* (SfCAD) but does bind the cadherin receptor of *Helicoverpa zea* (HzCAD). The protein variants described here were first selected using PACE (see Example 1) with an SP encoding TIC105 and host cells with an AP expressing a chimeric cadherin of *S. frugiperda* and *H. zea* (Sf/HzCAD). Following the first round of PACE on Sf/HzCAD, variant SPs were evolved in two additional rounds of evolution on SfCAD.

TIC105 and its variants were tested for relative toxicity in insect cell-based assays. The toxicity to Sf9 cells expressing chimera Ci/Sf/Ci.Cadherin (SEQ ID NO:13) from *S. frugiperda* (fall armyworm) and *C. includens* (soybean looper), was measured by increased fluorescence intensity of SYTOX® Green nucleic acid stain. TIC105 amino acid sequence variants were pre-treated with trypsin to release the three-domain TIC105 toxic core (residues 29-619). TIC105 and its variants were tested in an insect cell-based assay. Each data point was the mean of three measurements subtracted from beta-glucanase background, with calculated standard deviation (SD) shown. PACE derived TIC105 variant IS0349 (SEQ ID NO:12) showed a relative fluorescence of 12705 (SD: 2892) compared to a value for unmodified TIC105 of −1229 (SD: 1349), indicating that the evolved toxin bound to the expressed cadherin.

To determine whether the modifications introduced into TIC105 variant IS0349 (SEQ ID NO:12) resulted in a loss of function relative to the ability of the modified TIC105 to bind normally to receptor *S. frugiperda* ABCc2, TIC105 and variants were also tested against Sf9 cells expressing the SfABCc2 transporter. PACE derived TIC105 variant IS0349 (SEQ ID NO:12) showed a relative fluorescence of 92513 (SD: 6571) compared to a value for unmodified TIC105 of 57201 (SD: 13372), indicating that binding to its natural receptor was retained by the polypeptides comprising the PACE-induced mutations.

Additional advantages and modifications of the examples will readily occur to those of ordinary skill in the art. The invention in its broader aspects is not limited to the specific details and representative embodiments shown in and described herein. Accordingly, various modifications may be made to the examples without departing from the spirit and scope of the general inventive concepts described.

What is claimed is:

1. A method for producing a modified pesticidal protein for controlling an infestation by a target pest in a crop, said method comprising:
   introducing a cadherin binding protein into a TIC105 protein to bind to a cadherin receptor of a target pest, wherein introducing the cadherin binding protein comprises inserting the amino acid sequence of SEQ ID NO:9 in place of three residues from G342 to A344 of the TIC105 protein comprising SEQ ID NO:8, and producing the protein;
   wherein the target pest is selected from the group consisting of fall armyworm, cabbage looper, and soybean looper.

2. The method of claim 1, further comprising providing the modified pesticidal protein within the diet of the target pest.

3. The method of claim 1, further comprising topically applying the modified pesticidal protein to the crop or the target pest.

4. The method of claim 1, further comprising expressing the modified pesticidal protein in a crop plant to control infestation of the target pest.

5. The method of claim 4, wherein the modified pesticidal protein is encoded by a polynucleotide molecule incorporated in the genome of said plant.

6. The method of claim 2, further comprising providing to the target pest a pesticidal agent that is different from the modified pesticidal protein and is selected from the group consisting of a bacterial toxin, a plant toxin, an arachnid toxin, a venom toxin, and a dsRNA targeting for suppression of an essential gene in said target pest.

7. The method of claim 6, wherein said pesticidal agent is selected from the group consisting of Cry1A, Cry1Aa, Cry1Ab, Cry1A.105, Cry1B, Cry1Bb1, Cry1C, Cry1Ca, Cry1C amino acid sequence variants, Cry1D, Cry1Da, Cry1D amino acid sequence variants, Cry1E, Cry1F, Cry1Fa, Cry1G, Cry1H, Cry1I, Cry1J, Cry1K, Cry1L, Cry2A, Cry2Aa, Cry2Ab, Cry2Ae, Cry3, Cry3Aa, Cry3A amino acid sequence variants, Cry3B, Cry3Bb, Cry3Bb amino acid sequence variants, Cry4B, Cry5, Cry6, Cry7, Cry8, Cry9, Cry15, Cry34, Cry35, Cry43A, Cry43B, Cry51Aa1, ET29, ET33, ET34, ET35, ET66, ET70, Cry1A.105, TIC400, TIC407, TIC417, TIC431, TIC800, TIC807, TIC834, TIC853, TIC901, TIC1201, TIC1415, TIC3131, VIP3A, VIP3B, 5307, Axmi184, Axmi205, eHIP toxin proteins, insecticidal DIG proteins, venom proteins, and the insecticidal core toxin of each of the foregoing.

8. The method of claim 6, wherein:
   a) the pesticidal agent is toxic to the same pest as the modified pesticidal protein; or
   b) the pesticidal agent is toxic to a different pest than the modified pesticidal protein.

9. The method of claim 3, wherein the crop comprises a monocotyledonous plant selected from the group consisting of rice, wheat, barley, grasses, bentgrass, sugarcane, oats, sorghum, chives, shallots, and corn.

10. The method of claim 3, wherein the crop comprises a dicotyledonous plant selected from the group consisting of cotton, canola, soybean, beans, sugarbeet, alfalfa, vegetables, fruits, curcubits, melons, pigeonpea, peppers, and peanut.

* * * * *